United States Patent
Bai et al.

(10) Patent No.: US 9,655,941 B2
(45) Date of Patent: May 23, 2017

(54) COMPOSITION COMPRISING CENTIPEDE GRASS EXTRACTS OR FRACTIONS THEREOF AS ACTIVE INGREDIENTS

(71) Applicant: Korea Atomic Energy Research Institute, Daejeon (KR)

(72) Inventors: Hyoungwoo Bai, Jeongeup-si (KR); Byung Yeoup Chung, Gochang-eup (KR); Seung Sik Lee, Jeongeup-si (KR); Sungbeom Lee, Jeongeup-si (KR)

(73) Assignee: Korea Atomic Energy Research Institute, Daejeon (KR)

( * ) Notice: Subject to any disclaimer, the term of this patent is extended or adjusted under 35 U.S.C. 154(b) by 0 days.

(21) Appl. No.: 14/435,127

(22) PCT Filed: Nov. 26, 2012

(86) PCT No.: PCT/KR2012/010024
§ 371 (c)(1),
(2) Date: Apr. 10, 2015

(87) PCT Pub. No.: WO2014/042316
PCT Pub. Date: Mar. 20, 2014

(65) Prior Publication Data
US 2015/0265667 A1   Sep. 24, 2015

(30) Foreign Application Priority Data

Sep. 17, 2012  (KR) .................. 10-2012-0102684
Sep. 20, 2012  (KR) .................. 10-2012-0104487

(51) Int. Cl.
A61K 36/899   (2006.01)

(52) U.S. Cl.
CPC ........ *A61K 36/899* (2013.01); *A61K 2236/33* (2013.01); *A61K 2236/331* (2013.01); *A61K 2236/333* (2013.01); *A61K 2236/35* (2013.01); *A61K 2236/39* (2013.01)

(58) Field of Classification Search
None
See application file for complete search history.

(56) References Cited

FOREIGN PATENT DOCUMENTS

| | | |
|---|---|---|
| CN | 1219403 | 6/1999 |
| KR | 1020090111509 | 11/2009 |
| KR | 1020100038389 | 4/2010 |

OTHER PUBLICATIONS

Badaboina et al. (2013) BMC Complementary and Alternative Medicine, 13: 350.*
Website document entitled: "Overweight and Obesity Statistics" (available at https://www.niddk.nih.gov/health-information/health-statistics/Pages/overweight-obesity-statistics.aspx). Downloaded from website Aug. 22, 2016.*
Website document entitled: "Type 2 Diabetes and Obesity: Twin Epidemics" (available at https://asmbs.org/resources/weight-and-type-2-diabetes-after-bariatric-surgery-fact-sheet). Downloaded from website Aug. 22, 2016.*
Lee et al. (2010) Molecules 15, 8251-8259.*
Park et al. (2012) BMC Complemenatry and Alternative Medicine, 12: 230.*
Raskin et al. (2004) Current Pharmaceutical Design, 10, 3419-3429.*
Revilla et al. (1998) J. Agric. Food Chem. 46, 4592-4597.*
Steppan et al. (2001) Nature vol. 409, 307-312.*
Bai et al. (May 2012) "Drastic Enhancement of Maysin and Maysin Derivatives Contents in the Centipedegrass Extracts by Different Stresses," In: 2012 International Conference on Biomedical Engineering and Biotechnology, pp. 187-189.
Cheng et al. (Jul. 2009) "Neuroprotective Effect of Luteolin on Amyloid β Protein (25-35)-Induced Toxicity in Cultured Rat Cortical Neurons," Phytotherapy Research 24:S102-S108.
Daedeoknet News (Jul. 2012) "Korea Atomic Energy Research Institute (KAERI) Developed Cosmetics Using Ingredients of the Grass," http://www.hellodd.com/Kr/DD_News/Article_View.asp?Mark=38417, 1 page. (Korean language with English translation).
Kim et al. (Feb. 2012) "Protective Effects of Maysin, a Natural Plant Product on Nonalcoholic Fatty Liver Disease in Diabetic db/db Mice," 2012 Winter Symposium of the Korean Association for Laboratory Animal Science, pp. 111.
International Search Report for PCT/KR2012/010024, Apr. 29, 2013, 8 pp.

* cited by examiner

*Primary Examiner* — Chris R Tate
*Assistant Examiner* — Russell Fiebig
(74) *Attorney, Agent, or Firm* — Lathrop & Gage LLP

(57) ABSTRACT

The present invention relates to a pharmaceutical composition for preventing or treating diabetes or dementia, comprising centipede grass (*Eremochloa ophiuroides*) extracts as an active ingredient. It has been identified from animal tests that the centipede grass extracts, fractions thereof, and active fractions separated from the said fractions effectively regulate blood glucose levels, and inhibit the activity of amyloid-β(Aβ) which is involved in the formation of amyloid plaques that might cause dementia. Thus, the extracts, the fractions thereof, and the active fractions separated from the said fractions can be effectively used in a composition for preventing and treating diabetes or dementia, in a functional food for preventing or improving diabetes or dementia, and in a pharmaceutical composition or health food for blood glucose regulation.

4 Claims, 22 Drawing Sheets

COMPOSITION COMPRISING CENTIPEDE GRASS EXTRACTS OR FRACTIONS THEREOF AS ACTIVE INGREDIENTS

CROSS-REFERENCE TO RELATED APPLICATIONS

This application is a U.S. National Stage Application filed under 35 U.S.C. §371 of International Application No. PCT/KR2012/010024, filed Nov. 26, 2012, which claims the benefit of Korean Application No. KR 10-2012-0104487, filed Sep. 20, 2012, and Korean Application No. KR 10-2012-0102684, filed Sep. 17, 2012. These applications are hereby incorporated by reference in their entireties.

BACKGROUND OF THE INVENTION

1. Field of the Invention

The present invention relates to a pharmaceutical composition for preventing or treating diabetes or dementia, comprising centipede grass (*Eremochloa ophiuroides*) extracts or the fractions thereof as an active ingredient.

2. Description of the Related Art

According to the rapid economic development and improvement of life style and westernization, it is good to see the desirable physical development, but at the same time disease pattern has also been changed into the westernized adult diseases caused by excessive intake of high-caloric diet, lack of exercise, and stress accompanied by the advancement of industrial society. The most representative adult diseases are liver disease, hypertension, diabetes, obesity, and hyperlipidemia, etc.

One of those representative adult diseases, diabetes, is a non-communicable chronic disease, which is caused by the lack or malfunction of insulin secreted in β cells of pancreas so that glucose cannot be used as an energy source in vivo and stays in the blood at high concentration to be excreted later in urine. Diabetes is divided according to the cause and the method for treating symptoms largely into two groups; which are insulin dependent diabetes mellitus (IDDM) and non-insulin dependent diabetes mellitus (NIDDM). In Korea, at least 95% of diabetes patients are NIDDM patients. Diabetes has been a serious social issue not because the disease itself is a serious one but because it accompanies complications such as diabetic neuropathy, retinopathy, cataract, and nephropathy that can be a barrier for the patients to lead an ordinary life and further causes a lethal result.

The most common anti-diabetic agents are mainly divided into two groups; which are oral hypoglycemic agents and insulin injections. In general, the insulin injections are recommended for insulin dependent diabetes patients lack of insulin secretion in vivo; gestational diabetes patients; and non-insulin dependent diabetes patients having difficulty in regulating blood glucose by oral hypoglycemic agents. In the meantime, the oral hypoglycemic agents are recommended for non-insulin dependent patients having difficulty in regulating blood glucose with diet therapy and exercise. The oral hypoglycemic agents are exemplified by sulfonylurea-based drugs and biguanide-based drugs.

The sulfonylurea-based drugs, which are exemplified by glipizide, gliclazide, gliquidone, glibenclamide, and chlorpropamide, play a role in accelerating insulin secretion in pancreas, but they cannot be used for those insulin dependent diabetes patients particularly characterized by non-secretion of insulin and only can be applied to those who are non-insulin dependent patients showing comparatively weak insulin secretion. The said drugs cannot be used for woman of childbearing age because of the risk of giving birth to a deformed child, miscarriage, and stillbirth, etc. Most sulfonylurea-based drugs are metabolized in the liver and then excreted through the kidney, suggesting that the administration to the renal or liver dysfunction patients has to be carefully considered.

The biguanide-based drugs exemplified by metformin have been known to increase insulin secretion in pancreas even though the drug mechanism has not been disclosed, yet. Hypoglycemic effect of the biguanide-based drug is lower than that of the sulfonylurea-based drug but the risk of causing hypoglycemia is also low. However, these drugs could cause side effects in digestive system carrying nausea, vomiting, diarrhea, and rash, etc in the early stage of treatment, and also cause lactic acidosis that might be a lethal side effect threatening a life. So, these drugs are allowed for the experimental use only in US.

Since the recent sulfonylurea-based drugs or biguanide-based drugs have problems or side effects, it is requested to develop a safer hypoglycemic agent with less side effects that can be advantageously used for treating the increasing diabetes patients domestically or internationally.

The recent synthetic anti-diabetic agents also have serious side effects and cause drug resistance as well with reducing the drug effect. Therefore, studies have been actively going on to develop or screen a novel material from natural sources that has anti-diabetic activity, instead of using those chemosynthetic anti-diabetic agents.

In the normal brain, neurofibrillary tangles and amyloid plaques are not observed. However, in the brain of dementia patient, neurofibrillary tangles are formed in neurons and amyloid plaques are formed outside of the neurons.

Not only the formation of neurofibrillary tangles and amyloid plaques, which are major causes and characteristics of dementia, but also genetic factors such as presenilin, beta-APP (beta-amyloid precursor protein), and ApoE (apolipoprotein) and other factors are all involved in the development of dementia. Among these, particularly tau protein and beta-amyloid inducing the formation of amyloid plaques and neurofibrillary tangles are believed to be the most important factors. Beta amyloid plaque, one of the representative characteristics of dementia (Alzheimer's disease), is found in between neurons and is the result of the accumulation of abnormal beta-amyloid. The increase of beta-amyloid and hyperphosphorylated tau protein in brain neurons can reduce the level of acetylcholine that is a neurotransmitter involved in memory and learning. So, dementia patients display poor memory and judgment thereby. Dementia is a neurodegenerative disease developed with aging, particularly caused by the selective apoptosis of neurons.

APP (amyloid precursor protein) is generated by the gene located in chromosome #21, which is a glycoprotein belonging to type I transmembrane family expressed in neuroglial cells and neuroblasts. As a cell surface receptor, APP regulates cell adhesion and neurite growth and is also involved in cell signaling pathway to accelerate the growth of neurons and to protect thereof. The mutation of APP is a cause of familial dementia (familial Alzheimer's disease). The abnormal APP mediated Aβ generation is the most crucial pathological step of dementia. Aβ is a protein having the molecular weight of 4 kD which is generated when APP is digested with the proteases called β and γ secretase. Particularly, the mutation of prosenilin (PS1) and PS2 affecting the degradation of APP by the secretase or the mutation of APP induces the abnormal accumulation of A. Aβ is a water-soluble protein generated in the course of normal cell metabolism and then secreted into extracellular space.

APP is a type 1 membrane protein, which plays an important role in the development, differentiation, and survival of neurons. In normal APP metabolism, the generation of Aβ is blocked and non-amyloidogenic pathway progresses. At this time, the protease called secretase is the first one to act. APP NTF (sAPPα) and APP CTF (C83) are generated by α-secretase, which are cut by γ-secretase again to produce P3 that is a peptide shorter than Aβ and not deposited in senile plaque and APP intracellular domain (AICD) fragment. To generate Aβ which is the major component of senile plaque usually shown in dementia patients, APP is first cut by β-secretase to produce APP NTF (sAPPβ) and APP CTF (C99), leading to the amyloid synthesis pathway. The APP CTF (C99) previously digested with β-secretase is now cut again by γ-secretase, and the fragment produced thereby is deposited in the brain tissue to produce Aβ and AICD known to make senile plaque.

The activated β-secretase and γ-secretase increase the production of Aβ 1-42 and the increased Aβ40 and Aβ42 increase pre-fibrillar aggregates, resulting in the formation of amyloid plaque that is a cause of dementia.

To overcome the problem of the aggregation of amyloid plaque, it is necessary to develop a novel anti-dementia agent by using a natural bioactive material. The natural bioactive material is advantageous because it has less side effects than the chemosynthetic material and has excellent stability and safety resulted from the less longitudinal/chemical changes. Thus, studies have been focused on such natural plant resources that display pharmaceutical effect on dementia.

Centipede grass (*Eremochloa ophiuroides*) is warm-season turfgrass whose growth is late and creeping. This grass is perennial, which grows in a chunk of turf. Centipede grass belongs to Poaceae, and the scientific name thereof is *Eremochloa ophiuroides* (Munro) Hack. It is mainly distributed in China, East Asia, Indichina, Northeastern United States, Mesoamerica and Caribbean regions. It endures various kinds of soil but particularly prefers humid acidic soil and sandy soil with low fertility. In relation to its morphological characteristics, the leaf is 15~30 mm in length and 2~4 mm in width and is flat with a white mid vein. It does not have hairs except collar part and the tip of leaf is round. The stem has a compressed sheath and the roots are stolons having thin branches. The flower of it has a raceme in 3~5 inches. This raceme is purple and slightly flat-shaped and has two rows of spikelets. This plant is mainly used as lawn grass or turf. It can also be used as bird-feeds owing to its leafiness and good taste.

Studies have been focused on the use of centipede grass for the prevention and treatment of obesity, for the prevention and treatment of cancer, for the prevention of skin aging, and for skin whitening, etc. However, any statement saying which component of centipede grass has what kind of pharmaceutical effect has not been made yet. In particular, the effect of centipede grass in relation to diabetic disease and dementia has not been reported, yet.

In the course of study on the natural plants displaying an excellent treatment effect on diabetes, the present inventors confirmed that centipede grass extracts, fractions thereof, and active fragments separated from those fractions could efficiently regulate blood glucose, leading to the completion of the present invention by further confirming that the centipede grass, the fractions thereof, and the active fragments separated therefrom could be effectively used as a novel anti-diabetic agent.

The present inventors also studied to develop a natural plant extract for treating dementia. As a result, the present inventors confirmed that the centipede grass extract, the fractions thereof, and the active fragments separated from those fractions could inhibit the activity of amyloid-beta (Aβ) in the animal model. Thus, the present inventors proposed the centipede grass extract, the fractions thereof, and the active fragments separated therefrom could be efficiently used as an active ingredient for a composition for the prevention and treatment of dementia, leading to the completion of this invention.

SUMMARY OF THE INVENTION

It is an object of the present invention to provide a composition for the prevention and treatment of diabetes comprising centipede grass (*Eremochloa ophiuroides*) extracts or the fractions thereof as an active ingredient.

It is another object of the present invention to provide a pharmaceutical composition for the prevention and treatment of dementia comprising centipede grass (*Eremochloa ophiuroides*) extracts as an active ingredient.

To achieve the above objects, the present invention provides a composition for the prevention and treatment of diabetes comprising centipede grass (*Eremochloa ophiuroides*) extracts as an active ingredient.

The present invention also provides a pharmaceutical composition for the prevention and treatment of diabetes comprising the organic solvent fractions prepared by extracting the centipede grass extract additionally with an organic solvent as an active ingredient.

The present invention further provides a health food for the prevention or improvement of diabetes comprising centipede grass extracts, the fractions thereof prepared by extracting the centipede grass extract additionally with an organic solvent, or the active fractions extracted from the acetate fraction of the centipede grass methanol extract by using methanol as an active ingredient.

The present invention also provides a pharmaceutical composition for the regulation of blood glucose comprising centipede grass extracts as an active ingredient.

The present invention also provides a health food for the regulation of blood glucose comprising centipede grass extracts as an active ingredient.

The present invention also provides a pharmaceutical composition for the prevention and treatment of dementia comprising centipede grass (*Eremochloa ophiuroides*) extracts as an active ingredient.

The present invention also provides a pharmaceutical composition for the prevention and treatment of dementia comprising the organic solvent fractions prepared by extracting the centipede grass extract additionally with an organic solvent as an active ingredient.

The present invention also provides a health food for the prevention and improvement of dementia comprising centipede grass extracts as an active ingredient.

The present invention also provides a health food for the prevention and improvement of dementia comprising the organic solvent fractions prepared by extracting the centipede grass extract additionally with an organic solvent as an active ingredient.

The present invention also provides a method for treating diabetes containing the step of administering the fractions prepared by extracting the centipede grass extract additionally with an organic solvent or the active fractions extracted from the acetate fraction of the centipede grass methanol extract by using methanol to a subject having diabetes.

The present invention also provides a method for preventing diabetes containing the step of administering the centipede grass extracts, the fractions prepared by extracting the centipede grass extract additionally with an organic solvent or the active fractions extracted from the acetate fraction of the centipede grass methanol extract by using methanol to a subject.

The present invention also provides a use of the centipede grass extracts, the fractions prepared by extracting the centipede grass extract additionally with an organic solvent or the active fractions extracted from the acetate fraction of the centipede grass methanol extract by using methanol for the preparation of a pharmaceutical composition for the prevention or treatment of diabetes.

The present invention also provides a use of the centipede grass extracts, the fractions prepared by extracting the centipede grass extract additionally with an organic solvent or the active fractions extracted from the acetate fraction of the centipede grass methanol extract by using methanol for the preparation of a health food for the prevention or improvement of diabetes.

The present invention also provides a method for regulating blood glucose using the centipede grass extracts, the fractions prepared by extracting the centipede grass extract additionally with an organic solvent or the active fractions extracted from the acetate fraction of the centipede grass methanol extract by using methanol.

The present invention also provides a use of the centipede grass extracts, the fractions prepared by extracting the centipede grass extract additionally with an organic solvent or the active fractions extracted from the acetate fraction of the centipede grass methanol extract by using methanol for the preparation of a pharmaceutical composition for regulating blood glucose.

The present invention also provides a use of the centipede grass extracts, the fractions prepared by extracting the centipede grass extract additionally with an organic solvent or the active fractions extracted from the acetate fraction of the centipede grass methanol extract by using methanol for the preparation of a health food for regulating blood glucose.

The present invention also provides a method for treating dementia containing the step of administering the centipede grass extracts, the fractions prepared by extracting the centipede grass extract additionally with an organic solvent or the active fractions extracted from the acetate fraction of the centipede grass methanol extract by using methanol to a subject having dementia.

The present invention also provides a method for preventing dementia containing the step of administering the centipede grass extracts, the fractions prepared by extracting the centipede grass extract additionally with an organic solvent or the active fractions extracted from the acetate fraction of the centipede grass methanol extract by using methanol to a subject.

The present invention also provides a use of the centipede grass extracts, the fractions prepared by extracting the centipede grass extract additionally with an organic solvent or the active fractions extracted from the acetate fraction of the centipede grass methanol extract by using methanol for the preparation of a pharmaceutical composition for the prevention or treatment of dementia.

In addition, the present invention provides a use of the centipede grass extracts, the fractions prepared by extracting the centipede grass extract additionally with an organic solvent or the active fractions extracted from the acetate fraction of the centipede grass methanol extract by using methanol for the preparation of a health food for the prevention or improvement of dementia.

Advantageous Effect

The centipede grass extracts, the fractions thereof, or the active fractions separated from those fractions of the present invention are natural materials having no toxicity which can regulate blood glucose efficiently, so that they can be used as a composition for preventing or treating diabetes or applied to a health functional food for preventing or treating diabetes.

In this invention, the centipede grass (*Eremochloa ophiuroides*) extracts and the active fractions thereof were confirmed in animal tests to inhibit the activity of amyloid-β (Aβ) involved in the formation of amyloid plaques that is a cause of dementia, suggesting that they could be efficiently used as an active ingredient for a composition for preventing or treating dementia.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
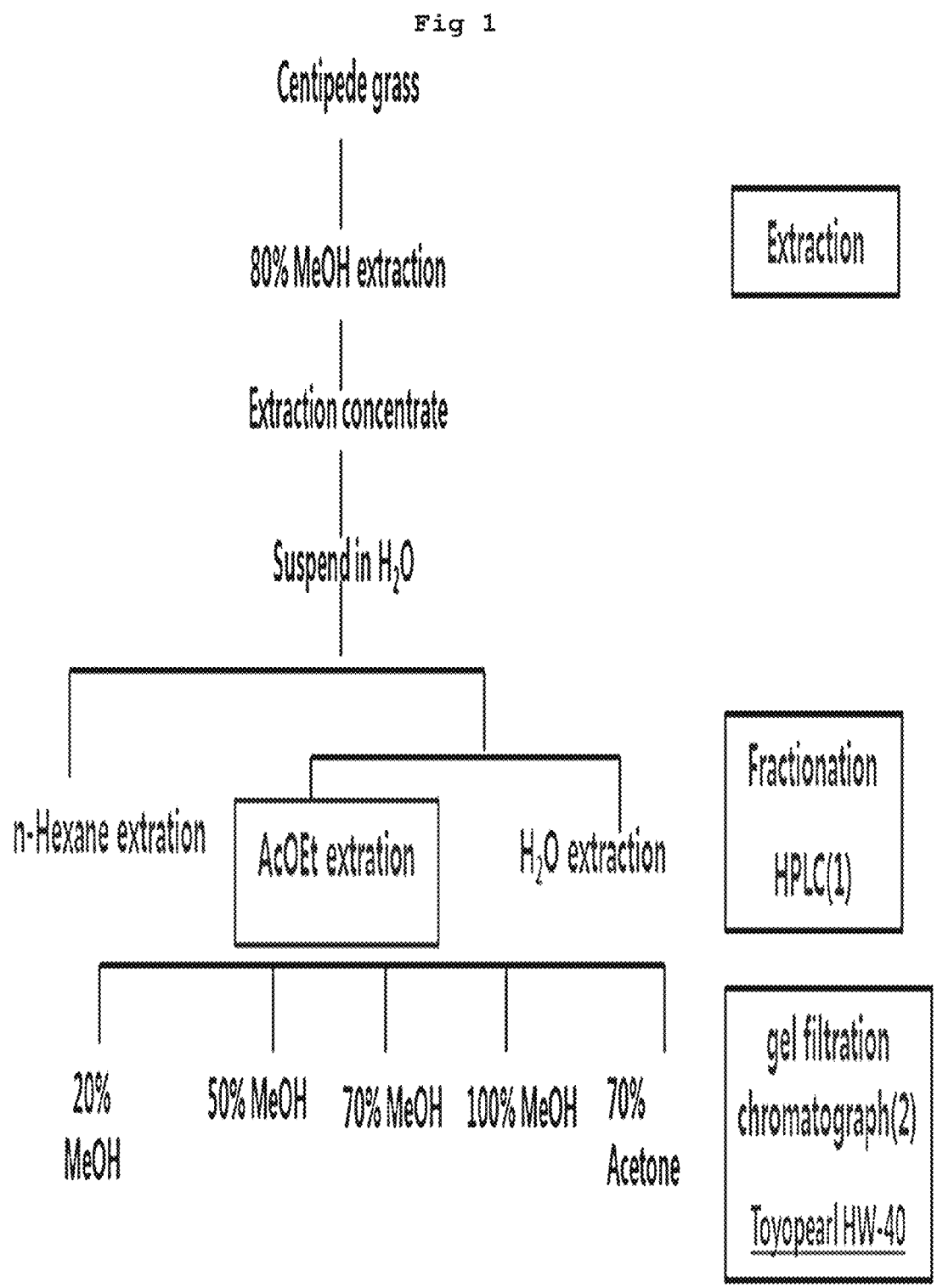
FIG. 1 is a diagram illustrating the preparation processes of the centipede grass extracts, the fractions thereof, and the active fractions separated from those fractions of the present invention.

Hereinafter, the present invention is described in detail.

The present invention provides a composition for the prevention and treatment of diabetes comprising centipede grass (*Eremochloa ophiuroides*) extracts as an active ingredient.

The said centipede grass extract is preferably prepared by the below preparation method comprising the following steps, but not always limited thereto:

1) extracting centipede grass by adding an extraction solvent;

2) cooling the extract obtained in step 1) and filtering thereof; and 3) concentrating the extracted filtered in step 2) under reduced pressure.

In the above method, the centipede grass of step 1) is either cultivated or purchased. Leaves, stems, or roots of the centipede grass can be used but the leaves are more preferred.

In the above preparation method, the extraction solvent of step 1) is preferably water, alcohol, or the mixture thereof. The said alcohol is preferably $C_1 \sim C_2$ lower alcohol. The lower alcohol herein is preferably ethanol or methanol, and more preferably methanol, but not always limited thereto. The extraction method is preferably shaking extraction or reflux extraction, but not always limited thereto. The extraction solvent is added to the dried centipede grass at the volume of 2~10 times the total volume of the centipede grass and more preferably added at the volume of 10 times, but not always limited thereto. The extraction temperature is preferably 50° C.~120° C., and more preferably 40° C.~45° C., but not always limited thereto. The extraction hours are preferably 2~5 days, but not always limited thereto. And the extraction is preferably repeated 1~3 times, but not always limited thereto.

In this method, the concentration under reduced pressure of step 3) is preferably performed by using a vacuum concentrator or a vacuum rotary evaporator, but not always limited thereto. The temperature for the concentration under reduced pressure is preferably 20° C.~60° C., and more preferably 45° C.~55° C., but not always limited thereto. Drying is preferably performed by reduced-pressurized drying, vacuum drying, boiling drying, spray drying, or freeze drying, but not always limited thereto. The freeze drying is preferably performed at −50~−100° C., and more preferably at −70° C., but not always limited thereto.

In the above method, the centipede grass extract is preferably prepared by hot-water extraction, but not always limited thereto.

The present invention also provides a composition for the prevention and treatment of diabetes comprising the organic solvent fractions prepared by extracting the centipede grass extract additionally with an organic solvent as an active ingredient.

The fractions of the centipede grass extract or the active fractions separated from those fractions can be preferably prepared by the method comprising the following steps, but not always limited thereto:

1) preparing the organic solvent fractions by adding an organic solvent to the centipede grass extract; and 2) preparing the active fractions by performing column chromatography with the fractions of step 1).

In the above method, the organic solvent of step 1) is preferably n-hexane or ethylacetate, but not always limited thereto.

In the above method, the organic solvent fraction is preferably the ethylacetate fraction that is obtained from the additional extraction of the centipede grass methanol extract. Precisely, the centipede grass methanol extract is extracted by using n-hexane and the soluble layer is eliminated. Then, the remaining water layer is extracted by using ethylacetate. However, the fraction is not limited thereto.

In the above method, the column chromatography of step 2) can be performed with a filler selected from the group consisting of silica gel, sephadex, RP-18, polyamide, Toyopearl, and XAD resin for the separation and purification of the active fractions. If necessary, the column chromatography filled with a proper filler can be performed several times repeatedly.

In the above method, the ethylacetate fraction of the centipede grass extract of step 2) can be additionally loaded on the column chromatography, by which the active fractions can be separated by using methanol as an elution solvent. At this time, the methanol is preferably 20~70% methanol. Particularly, the present inventors loaded the centipede grass ethylacetate fraction on Flex-Colum™ (3 cm×25 cm) and Toyoperarl HW-40 (75 μm) column chromatography, to which 20, 50, or 70% methanol was added as an elution solvent. As a result, ethylacetate-20% methanol active fraction, ethylacetate-50% methanol active fraction, and ethylacetate-70% methanol active fraction were obtained.

To investigate the conversion of glucose into fat in adipocytes by the centipede grass ethylacetate-methanol fraction, the present inventors first examined whether or not the ethylacetate-50% and ethylacetate-70% methanol fractions could increase the glucose absorption of adipocytes by using an adipocyte cell line (3T3-L1 preadipocyte cell line). As a result, referring to the group treated with the low concentration of insulin as a standard, the accumulation of fat in adipocytes was approximately 300% increased in the group treated with 100 μg/ml of the ethylacetate-50% methanol fraction (see FIGS. 2 and 3). The hypoglycemic activity of the fractions obtained from the centipede grass extract in type II diabetic mice (db/db mice) was also investigated. As a result, the blood glucose of the group treated with the centipede grass ethylacetate-50% and ethylacetate-70% methanol fractions for 10 days was lowered 70~80% by that of the diabetes induced model. When the treatment of the sample was stopped, the level of blood glucose of the mouse began to increase again (see FIG. 4). Oral glucose tolerance test (OGTT) was performed to investigate the effect of the centipede grass ethylacetate-methanol fraction. As a result, the rapid blood glucose increase was suppressed approximately 25% in the group treated with the centipede grass ethylacetate-methanol fraction, compared with the comparative group, and 150 minutes later, the hypoglycemic effect was strengthened to 60%, compared with the comparative group (see FIGS. 5 and 6). Oral glucose tolerance test was performed this time with different doses of the centipede grass ethylacetate-methanol fraction. As a result, the group treated with the centipede grass ethylacetate-50% methanol fraction demonstrated that the rapid increase of blood glucose was suppressed at the level of 40% with a high dose of the fraction and maintained at the level of 60% with a low dose of the fraction 60 minutes after the administration, compared with the comparative group (see FIG. 7). In the meantime, intraperitoneal glucose tolerance test (IPGTT) was performed with different doses of the centipede grass ethylacetate-50% methanol fraction. As a result, the group treated with the centipede grass ethylacetate-50% methanol fraction at a high and a low concentrations demonstrated that the hypoglycemic effect was approximately 80% increased 2 hours later, compared with the comparative group (see FIG. 8). Oral glucose tolerance test was performed after the centipede grass ethylacetate-methanol fraction was administered intraperitoneally into the mouse. 4.5 hours later, the blood glucose of the control group mouse was maintained at the level of 400 mg/dL or up, but the blood glucose of the group treated with the centipede grass ethylacetate-50% methanol fraction was reduced to the level of 250 mg/dL or under. This result indicates that the hypoglycemic effect was increased approximately 60% in the experimental group, compared with the control group (see FIG. 9). The anti-diabetic activity of the centipede grass ethylacetate-methanol fraction was investigated in streptozotocin (STZ)-induced type I diabetic model. As a result, the blood glucose level of the group treated with the centipede grass ethylacetate-methanol fraction was reduced to the level of the normal group from the time point of 4.5 hours after the administration. However, the blood glucose level of the control group was still maintained high, precisely 150 mg/dL higher than that of the normal group even 6 hours later. The blood glucose level of the group treated with the centipede grass ethylacetate-methanol fraction 6 hours after the administration of glucose was 100% reduced, compared with the control group (see FIG. 10).

Therefore, it was confirmed that the centipede grass extracts, the fractions thereof, and the active fractions separated from those fractions could efficiently regulate blood glucose, so that they can be advantageously used for a composition for the prevention and treatment of diabetes, a health functional food for the prevention and improvement of diabetes, a pharmaceutical composition for the regulation of blood glucose, and a health food for the regulation of blood glucose.

According to the pharmaceutical composition for the prevention and treatment of diabetes of the present invention, the diabetes is preferably type I diabetes or type II diabetes, but not always limited thereto.

The present invention also provides a pharmaceutical composition for the regulation of blood glucose comprising centipede grass extracts as an active ingredient.

The said centipede grass extract is prepared by extracting centipede grass with water, $C_1$~$C_2$ lower alcohol, or the mixture thereof, but not always limited thereto.

The lower alcohol herein is preferably ethanol or methanol, but not always limited thereto.

The centipede grass extract is preferably prepared by hot-water extraction, but not always limited thereto.

The present invention further provides a health food for the prevention or improvement of diabetes comprising centipede grass (*Eremochloa ophiuroides*) extracts as an active ingredient.

It is also preferred for the composition to contain the active fractions as an active ingredient which are separated from the fractions obtained from the centipede grass extract by column chromatography.

In the health food for the prevention or improvement of diabetes of the present invention, the diabetes is preferably type I diabetes or type II diabetes, but not always limited thereto.

The present invention also provides a health food for the regulation of blood glucose comprising centipede grass (*Eremochloa ophiuroides*) extracts as an active ingredient.

The pharmaceutical composition of the present invention hardly has toxicity and side effects, so that it is safe even for a long term administration.

The centipede grass extracts, the fractions thereof, or the active fractions separated from the fractions can be added to the health food of the present invention as they are or as mixed with other food ingredients according to the conventional method well known to those in the art.

The food herein is not limited. For example, the centipede grass extracts, the fractions thereof, or the active fractions separated from the fractions can be added to meat, sausages, bread, chocolates, candies, snacks, cookies, pizza, ramyuns, flour products, gums, dairy products including ice cream, soups, beverages, tea, drinks, alcohol drinks and vitamin complex, etc, and in wide sense, almost every food applicable in the production of health food can be included.

The pharmaceutical composition of the present invention can additionally include any general excipient, disintegrating agent, sweetening agent, lubricant and flavor. The composition can be formulated in the forms of tablets, capsules, powders, granules, suspensions, emulsions, syrups, and other solutions by the conventional method.

Particularly, the pharmaceutical composition of the present invention can be formulated for oral administration, for example tablets, troches, lozenges, soluble or insoluble suspensions, powders, granules, emulsions, hard or soft capsules, syrups, or elixirs. For the formulation, binders such as lactose, saccharose, sorbitol, mannitol, starch, amylopectin, cellulose or gelatin; excipients like dicalcium phosphate; disintegrating agents such as corn starch or sweet potato starch; and lubricants such as magnesium stearate, calcium stearate, sodium stearylfumarate, or polyethyleneglycol wax can be included. For the preparation of capsules, liquid carriers like fatty oil can be additionally included.

The pharmaceutical composition of the present invention can be administered by orally or parenterally and the parenteral administration includes subcutaneous injection, intravenous injection, intramuscular injection and intrathoracic injection. To prepare the composition as a formulation for parenteral administration, the centipede grass extracts, the fractions thereof, or the active fractions separated from the fractions of the present invention are mixed with a stabilizer or a buffering agent to produce a solution or suspension, which is then formulated as ampoules or vials.

The effective dosage of the pharmaceutical composition of the present invention can be determined according to absorptiveness of the active ingredient, inactivation rate, excretion rate, age, gender, health condition and severity of a disease by those in the art. In the case of oral administration, the pharmaceutical composition can be administered by 0.0001~500 mg/kg per day for an adult, and more preferably by 0.001~100 mg/kg per day. The administration frequency is once a day or a few times a day.

The present invention also provides a pharmaceutical composition for the prevention and treatment of dementia comprising centipede grass (*Eremochloa ophiuroides*) extracts as an active ingredient.

The said centipede grass extract is prepared by extracting centipede grass with water, $C_1$~$C_2$ lower alcohol, or the mixture thereof, but not always limited thereto.

The lower alcohol herein is preferably ethanol or methanol, but not always limited thereto.

The centipede grass extract is preferably prepared by hot-water extraction, but not always limited thereto.

The present invention also provides a pharmaceutical composition for the prevention and treatment of dementia comprising the organic solvent fractions prepared by extracting the centipede grass extract additionally with an organic solvent as an active ingredient.

The organic solvent herein is preferably n-hexane or ethylacetate, but not always limited thereto.

The said organic solvent fraction is preferably the ethylacetate fraction that is prepared by the following processes, but not always limited thereto; extracting the centipede grass methanol extract again with n-hexane; eliminating the soluble layer; and extracting the remaining water layer with ethylacetate.

The composition preferably comprises the active fractions prepared by additional extracting the ethylacetate fraction of the centipede grass methanol extract using methanol, but not always limited thereto.

The methanol herein is preferably 20~70% methanol, but not always limited thereto.

The said dementia is preferably selected from the group consisting of Alzheimer's disease, vascular dementia, alcoholic dementia, Parkinson's disease, lewy body dementia, Pick's disease, Creutzfeldt disease, and Huntington's disease, but not always limited thereto.

The present inventors investigated the inhibition of oligo-polymerization of Aβ(1-42) peptide by the centipede grass extracts or the fractions thereof. As a result, Aβ peptide was aggregated in the control group not-treated with the centipede grass extract, while the oligo-polymerization of Aβ was inhibited in the group treated with the centipede grass extract (see FIG. 11). The inhibition of BACE1 activity by the centipede grass ethylacetate-methanol fraction was also investigated. As a result, the centipede grass extract ethylacetate-50% methanol, ethylacetate-70% methanol, and ethylacetate-100% methanol fractions all inhibited BACE1 activity (see FIG. 12). The inhibition of BACE1 activity by the centipede grass extract ethylacetate-100% methanol fraction was investigated. As a result, the ethylacetate-100% methanol fraction was confirmed to inhibit BACE1 activity (see FIG. 13). It was also investigated whether or not the centipede grass ethylacetate-70% methanol fraction could inhibit BACE1 activity, and the result confirmed that the fraction also inhibited BACE1 activity in the reaction sample (see FIG. 14). The inhibition of BACE1 activity by the centipede grass ethylacetate-50% methanol fraction was investigated and as a result the fraction was confirmed to inhibit BACE1 activity (see FIG. 15).

It was also investigated whether or not the centipede grass ethylacetate-70% methanol fraction had the effect of inhibiting the activity of the dementia inducing enzyme. As a result, the fraction was confirmed to inhibit cytotoxicity induced by amyloid-beta significantly (see FIG. 16). The dementia-related enzyme activity inhibiting effect of the centipede grass ethylacetate-50% methanol fraction was also investigated. As a result, the ethylacetate-50% methanol fraction significantly inhibited cytotoxicity caused by amyloid-beta (see FIG. 17). It was further investigated whether or not the centipede grass extract ethylacetate-50% methanol fraction could inhibit reactive oxygen species (ROS) that is another cause of dementia. As a result, the ethylacetate-50% methanol fraction significantly inhibited the generation of reactive oxygen species induced by amyloid-beta (see FIG. 18).

It was investigated whether or not the secretion of amyloid-beta in the cells over-expressing BACE1, the enzyme that produces APP and β-amyloid inducing dementia, was affected by the centipede grass extract ethylacetate-methanol fraction. As a result, the centipede grass ethylacetate-methanol fraction reduced the activity of BACE1, suggesting the decrease of the production of amyloid-beta (see FIG. 19). The centipede ethylacetate-methanol fraction was treated to APP/PS1 mice, followed by the investigation of liver toxicity. As a result, the levels of AST, ALT, and ALP in the control APP mice were not much different from those of the experimental group mice treated with the centipede grass ethylacetate-methanol fraction, suggesting that those levels were all in the normal range. Therefore, it was confirmed that the centipede grass ethylacetate-methanol fraction did not cause liver toxicity (see FIG. 20). To measure the expression of cytokine gene mRNA in APP mice and in the mice treated with the centipede ethylacetate-methanol fraction, the expressions of IL-1a, IFN-g, and IL-6 mRNA expressed in the spleen of the control APP mice were first measured. As a result, the levels of IL-1a, IFN-g, and IL-6 mRNA in the spleen of the experimental group mice treated with the centipede grass ethylacetate-methanol fraction were higher than those of the control APP mice (see FIG. 21). The immune activity, cytokine activity, and the expressions of INF-1β, IFN-γ, and amyloid-beta (Aβ) were all measured both in the control APP mice and the mice treated with the centipede ethylacetate-methanol fraction by enzyme immunoassay. As a result, those activity and levels were all higher in the experimental group mice treated with the centipede grass ethylacetate-methanol fraction (see FIG. 22). More particularly, in the groups respectively treated with the centipede ethylacetate-50% methanol fraction, the centipede ethylacetate-70% methanol fraction, and the centipede grass ethylacetate-100% methanol fraction, the cytokine level was higher, suggesting that the immune activity is higher in those groups treated with the centipede ethylacetate-methanol fractions (see FIG. 23). Also, the levels of INF-1β and INF-γ were all significantly higher (see FIG. 24) but the level of amyloid-beta was lower in those groups respectively treated with the centipede ethylacetate-50% methanol fraction, the centipede ethylacetate-70% methanol fraction, and the centipede grass ethylacetate-100% methanol fraction than those of the control APP mice (see FIG. 25).

The test animals were treated with the centipede grass ethylacetate-methanol fraction, followed by H-E staining. As a result, cell death signal was strongly observed in the hippocampus of the mice treated with the centipede grass ethylacetate-50% methanol and ethylacetate-100% methanol fractions, compared with APP mice, suggesting that apoptosis in the brain tissue was suppressed (see FIG. 26). The cell death signal was also strongly observed in the cortex of the mice treated with the centipede grass ethylacetate-50% methanol and ethylacetate-100% methanol fractions, compared with APP mice, suggesting that progressive degeneration was suppressed (see FIG. 27).

The test animals were treated with the centipede grass ethylacetate-methanol, followed by immunohistochemical analysis. As a result, Aβ was significantly reduced in the groups treated with the centipede grass ethylacetate-50% methanol and ethylacetate-100% methanol fractions (see FIG. 28). More particularly, Aβ was significantly reduced in the mice treated respectively with the centipede grass ethylacetate-50% methanol fraction, the centipede grass ethylacetate-70% methanol fraction, and the centipede grass ethylacetate-100% methanol fraction, suggesting that the centipede grass ethylacetate-methanol fractions could reduce the accumulation of amyloid-beta in the cortex of the brain (see FIG. 29).

Therefore, it was confirmed that the centipede grass extracts, the fractions thereof, and the active fractions separated from the fractions had the Aβ activity inhibiting effect in the animal test, so that they could be used efficiently for a composition for the prevention and treatment of dementia and for a health food for the prevention or improvement of dementia.

The pharmaceutical composition of the present invention hardly has toxicity and side effects, so that it is safe even for a long term administration.

The pharmaceutical composition of the present invention can additionally include any general excipient, disintegrating agent, sweetening agent, lubricant and flavor. The composition can be formulated in the forms of tablets, capsules, powders, granules, suspensions, emulsions, syrups, and other solutions by the conventional method.

Particularly, the pharmaceutical composition of the present invention can be formulated for oral administration, for example tablets, troches, lozenges, soluble or insoluble suspensions, powders, granules, emulsions, hard or soft capsules, syrups, or elixirs. For the formulation, binders such as lactose, saccharose, sorbitol, mannitol, starch, amylopectin, cellulose or gelatin; excipients like dicalcium phosphate; disintegrating agents such as corn starch or sweet potato starch; and lubricants such as magnesium stearate, calcium stearate, sodium stearylfumarate, or polyethyleneglycol wax can be included. For the preparation of capsules, liquid carriers like fatty oil can be additionally included.

The pharmaceutical composition of the present invention can be administered by orally or parenterally and the parenteral administration includes subcutaneous injection, intravenous injection, intramuscular injection and intrathoracic injection. To prepare the composition as a formulation for parenteral administration, the centipede grass extracts, the fractions thereof, or the active fractions separated from the fractions of the present invention are mixed with a stabilizer or a buffering agent to produce a solution or suspension, which is then formulated as ampoules or vials.

The effective dosage of the pharmaceutical composition of the present invention can be determined according to absorptiveness of the active ingredient, inactivation rate, excretion rate, age, gender, health condition and severity of a disease by those in the art. In the case of oral administration, the pharmaceutical composition can be administered by 0.0001~500 mg/kg per day for an adult, and more preferably by 0.001~100 mg/kg per day. The administration frequency is once a day or a few times a day.

The present invention also provides a health food for the prevention and improvement of dementia comprising centipede grass (*Eremochloa ophiuroides*) extracts as an active ingredient.

The said centipede grass extract is prepared by extracting centipede grass with water, $C_1$~$C_2$ lower alcohol, or the mixture thereof, but not always limited thereto.

The lower alcohol herein is preferably ethanol or methanol, but not always limited thereto.

The centipede grass extract is preferably prepared by hot-water extraction, but not always limited thereto.

The present invention also provides a health food for the prevention and improvement of dementia comprising the organic solvent fractions prepared by extracting the centipede grass extract additionally with an organic solvent as an active ingredient.

The organic solvent herein is preferably n-hexane or ethylacetate, but not always limited thereto.

The composition preferably comprises the active fractions prepared by additional extracting the ethylacetate fraction of the centipede grass methanol extract using methanol, but not always limited thereto.

The said dementia is preferably selected from the group consisting of Alzheimer's disease, vascular dementia, alcoholic dementia, Parkinson's disease, lewy body dementia, Pick's disease, Creutzfeldt disease, and Huntington's disease, but not always limited thereto.

The centipede grass extracts, the fractions thereof, or the active fractions separated from the fractions can be added to the health food of the present invention as they are or as mixed with other food ingredients according to the conventional method well known to those in the art.

The food herein is not limited. For example, the centipede grass extracts, the fractions thereof, or the active fractions separated from the fractions can be added to meat, sausages, bread, chocolates, candies, snacks, cookies, pizza, ramyuns, flour products, gums, dairy products including ice cream, soups, beverages, tea, drinks, alcohol drinks and vitamin complex, etc, and in wide sense, almost every food applicable in the production of health food can be included.

The present invention also provides a method for treating diabetes containing the step of administering the fractions prepared by extracting the centipede grass extract additionally with an organic solvent or the active fractions extracted from the acetate fraction of the centipede grass methanol extract by using methanol to a subject having diabetes.

The present invention also provides a method for preventing diabetes containing the step of administering the centipede grass extracts, the fractions prepared by extracting the centipede grass extract additionally with an organic solvent or the active fractions extracted from the acetate fraction of the centipede grass methanol extract by using methanol to a subject.

The present invention also provides a use of the centipede grass extracts, the fractions prepared by extracting the centipede grass extract additionally with an organic solvent or the active fractions extracted from the acetate fraction of the centipede grass methanol extract by using methanol for the preparation of a pharmaceutical composition for the prevention or treatment of diabetes.

The present invention also provides a use of the centipede grass extracts, the fractions prepared by extracting the centipede grass extract additionally with an organic solvent or the active fractions extracted from the acetate fraction of the centipede grass methanol extract by using methanol for the preparation of a health food for the prevention or improvement of diabetes.

The present invention also provides a method for regulating blood glucose using the centipede grass extracts, the fractions prepared by extracting the centipede grass extract additionally with an organic solvent or the active fractions extracted from the acetate fraction of the centipede grass methanol extract by using methanol.

The present invention also provides a use of the centipede grass extracts, the fractions prepared by extracting the centipede grass extract additionally with an organic solvent or the active fractions extracted from the acetate fraction of the centipede grass methanol extract by using methanol for the preparation of a pharmaceutical composition for regulating blood glucose.

The present invention also provides a use of the centipede grass extracts, the fractions prepared by extracting the centipede grass extract additionally with an organic solvent or the active fractions extracted from the acetate fraction of the centipede grass methanol extract by using methanol for the preparation of a health food for regulating blood glucose.

The present invention also provides a method for treating dementia containing the step of administering the centipede grass extracts, the fractions prepared by extracting the centipede grass extract additionally with an organic solvent or the active fractions extracted from the acetate fraction of the centipede grass methanol extract by using methanol to a subject having dementia.

The present invention also provides a method for preventing dementia containing the step of administering the centipede grass extracts, the fractions prepared by extracting the centipede grass extract additionally with an organic solvent or the active fractions extracted from the acetate fraction of the centipede grass methanol extract by using methanol to a subject.

The present invention also provides a use of the centipede grass extracts, the fractions prepared by extracting the centipede grass extract additionally with an organic solvent or the active fractions extracted from the acetate fraction of the centipede grass methanol extract by using methanol for the preparation of a pharmaceutical composition for the prevention or treatment of dementia.

In addition, the present invention provides a use of the centipede grass extracts, the fractions prepared by extracting the centipede grass extract additionally with an organic solvent or the active fractions extracted from the acetate fraction of the centipede grass methanol extract by using methanol for the preparation of a health food for the prevention or improvement of dementia.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Preparation of Centipede Grass Extract

<1-1> Preparation of Centipede Grass Methanol Extract

The centipede grass seeds were purchased from Fukukaen Nursery and Blub Co. Ltd, Japan, which grew in the field at Advanced Radiation Technology Institute, Korea Atomic Energy Research Institute, Jeongeup, Korea. Leaves were collected from the grown centipede grass. The obtained leaves were stored at −80° C. 5 kg of the centipede grass leaves were mixed with 20 l of 100% methanol (MeOH), and the mixture was grinded in a mixer. Precipitation was induced at room temperature for 3 days. The obtained extract was concentrated under reduced pressure at 50° C. As a result, 210 g of centipede grass methanol extract was prepared.

<1-2> Preparation of Centipede Grass Ethanol Extract

The centipede grass seeds were purchased from Fukukaen Nursery and Blub Co. Ltd, Japan, which grew in the field at Advanced Radiation Technology Institute, Korea Atomic Energy Research Institute, Jeongeup, Korea. Leaves were collected from the grown centipede grass. The obtained leaves were stored at −80° C. 5 kg of the centipede grass leaves were mixed with 20 l of 100% ethanol (EtOH), and the mixture was grinded in a mixer. Precipitation was induced at room temperature for 3 days. The obtained extract was concentrated under reduced pressure at 50° C. As a result, 203 g of centipede grass ethanol extract was prepared.

<1-3> Preparation of Centipede Grass Water Extract

The centipede grass seeds were purchased from Fukukaen Nursery and Blub Co. Ltd, Japan, which grew in the field at Advanced Radiation Technology Institute, Korea Atomic Energy Research Institute, Jeongeup, Korea. Leaves were collected from the grown centipede grass. The obtained leaves were stored at −8° C. 5 kg of the centipede grass leaves were mixed with 20 l of water, and the mixture was grinded in a mixer. Precipitation was induced at room temperature for 3 days. The obtained extract was concentrated under reduced pressure at 50° C. As a result, 198 g of centipede grass water extract was prepared.

<1-4> Preparation of Centipede Grass Hot-Water Extract

The centipede grass seeds were purchased from Fukukaen Nursery and Blub Co. Ltd, Japan, which grew in the field at Advanced Radiation Technology Institute, Korea Atomic Energy Research Institute, Jeongeup, Korea. Leaves were collected from the grown centipede grass. The obtained leaves were stored at −8° C. 40 g of the centipede grass leaves were mixed with 40 l of water, followed by precipitation at 90° C. for 6 hours. As a result, 87 g of centipede grass hot-water extract was prepared.

Example 2: Preparation of Centipede Grass Fraction

The centipede grass methanol extract obtained in Example <1-1> was fractionated using organic solvents according to the polarity.

<2-1> Preparation of n-Hexane Fraction

First, as shown in FIG. 1, the centipede grass 100% MeOH extract was concentrated under reduced pressure, which was suspended in water, followed by extraction using n-hexane, the less polar solvent.

<2-2> Preparation of Ethylacetate Fraction

The water layer of the n-hexane fraction obtained in Example <2-1> was fractionated again with ethylacetate (EtOAc).

<2-3> Preparation of Water Fraction

Upon completion of the fractionation using n-hexane and ethylacetate, as described in Example <2-2>, the soluble fraction was lastly obtained by using water. Each solvent extraction fraction was concentrated under reduced pressure and then dried. As a result water fraction was obtained (21 g).

Example 3: Preparation of Centipede Grass Active Fraction

<3-1> Preparation of Ethylacetate-20% Methanol Fraction

The ethylacetate fraction obtained in Example 2 was mixed with 20% methanol used as an elution solvent, followed by column chromatography using Flex-Colum™ (3 cm×25 cm) and Toyoperarl HW-40 (75 μm). As a result, 9.41 g of ethylacetate-20% methanol active fraction was obtained.

<3-2> Preparation of Ethylacetate-50% Methanol Fraction

The ethylacetate fraction obtained in Example 2 was mixed with 50% methanol used as an elution solvent, followed by column chromatography using Flex-Colum™ (3 cm×25 cm) and Toyoperarl HW-40 (75 μm). As a result, 5.74 g of ethylacetate-50% methanol active fraction was obtained.

<3-3> Preparation of Ethylacetate-70% Methanol Fraction

The ethylacetate fraction obtained in Example 2 was mixed with 70% methanol used as an elution solvent, followed by column chromatography using Flex-Colum™ (3 cm×25 cm) and Toyoperarl HW-40 (75 μm). As a result, 1 g of ethylacetate-70% methanol active fraction was obtained.

<3-4> Analysis of the Components of Ethylacetate-30% Methanol and 70% Methanol Fractions Among the components of the ethylacetate-30% methanol and 70% methanol fractions, particularly the content of masyin and its derivatives was analyzed. Particularly, 20 μl of sample solution was loaded in Agilent Technologies 1200 series HPLC, and the mixture of 1% formic acid (solution A) and 100% methanol (solution B) was used as a moving phase. The moving phase proceeded to the combined step; linear gradient from 100:0 (solution A:B) to 50:50 for 30 minutes; and then linear gradient from 50:50 to 0:100 for 60 minutes, for the elution of those components of the fraction. The flow rate was 0.5 ml/min and the eluted compound was detected at $OD_{360}$. The contents of the eluted maysin and its derivatives are presented in Table 1.

TABLE 1

| Compound (% of powder mg) | 50% | 70% |
|---|---|---|
| Luteolin | 0.1938 | 1.6864 |
| Isoorientin | 3.1703 | 13.9925 |
| Rhamnosylisoorientin (with Orientin) | 1.8745 | 13.6534 |
| Derhamnosylmaysin | 20.2102 | 9.4434 |
| Maysin | 14.0661 | 19.2835 |
| Total | 39.5151 | 58.0593 |

Experimental Example 1: Conversion of Glucose to Fat in Adipocytes by Centipede Grass Ethylacetate-Methanol Fraction The present inventors investigated whether or not the ethylacetate-50% methanol and ethylacetate-70% methanol fractions could increase the glucose absorption of adipocytes by using 3T3-L1 preadipocyte cell line. Particularly, the preadipocyte cell line was purchased from American Type culture Collect (ATCC). The preadipocytes (3T3-L1) were distributed in a 6-well plate at the density of $1 \times 10^6$ cells/well, followed by culture in a $CO_2$ incubator for 24 hours until the confluency reached 90%. The medium was discarded and another medium helpful for the increase of adipocyte differentiation was added, followed by inducing adipocyte differentiation for 48 hours. The medium helpful for the increase of adipocyte differentiation above was DMEM supplemented with 10% FBS, 0.5 mM 3-isobutyl-1-methylxanthine (IBMX), 10 nm/ml insulin, and 1 μM dexamethasone. Once 3T3-L1 cells were differentiated into adipocytes, the adipocytes were respectively treated with the centipede grass crude extract, the negative control, the ethylacetate-50% methanol and ethylacetate-70% methanol fractions in the medium supplemented with a low concentration of insulin. When glucose flew in the adipocytes, it was accumulated as fat through glycometabolism. At this time, the amount of the accumulated fat was measured via Oil-Red-O staining. The Oil Red-O staining solution is a fat (particularly in adipocytes) specific reagent, which can stain the fat biosynthesized from the degradation of glucose. So, this reagent is advantageous for the analysis of the fat generation in each sample. The red stained solution was extracted by using iso-propanol, followed by measurement at $OD_{490}$.

Figure 2:
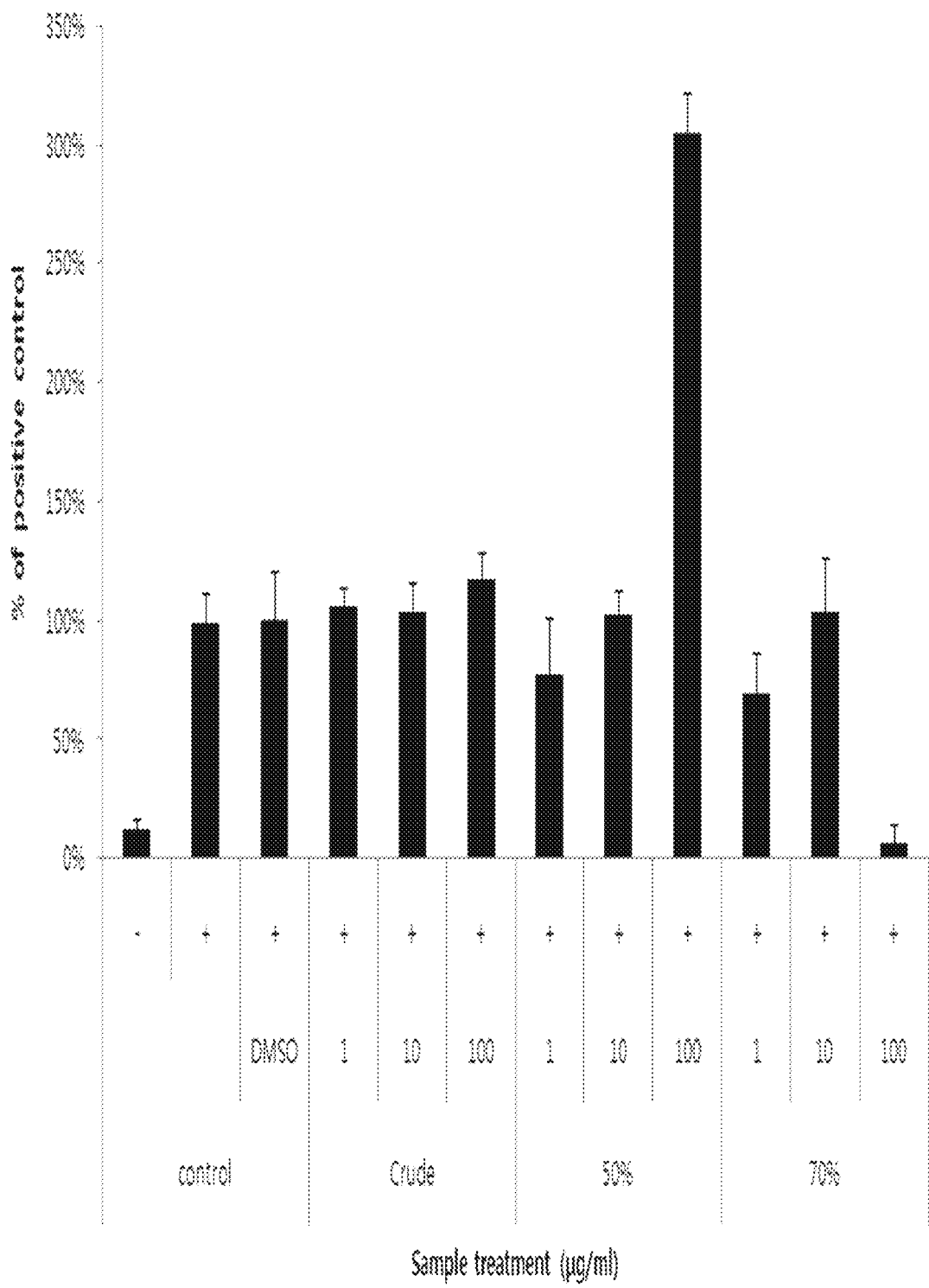
FIG. 2 is a diagram illustrating the fat accumulation of FIG. 3 in digitized values.
Figure 3:
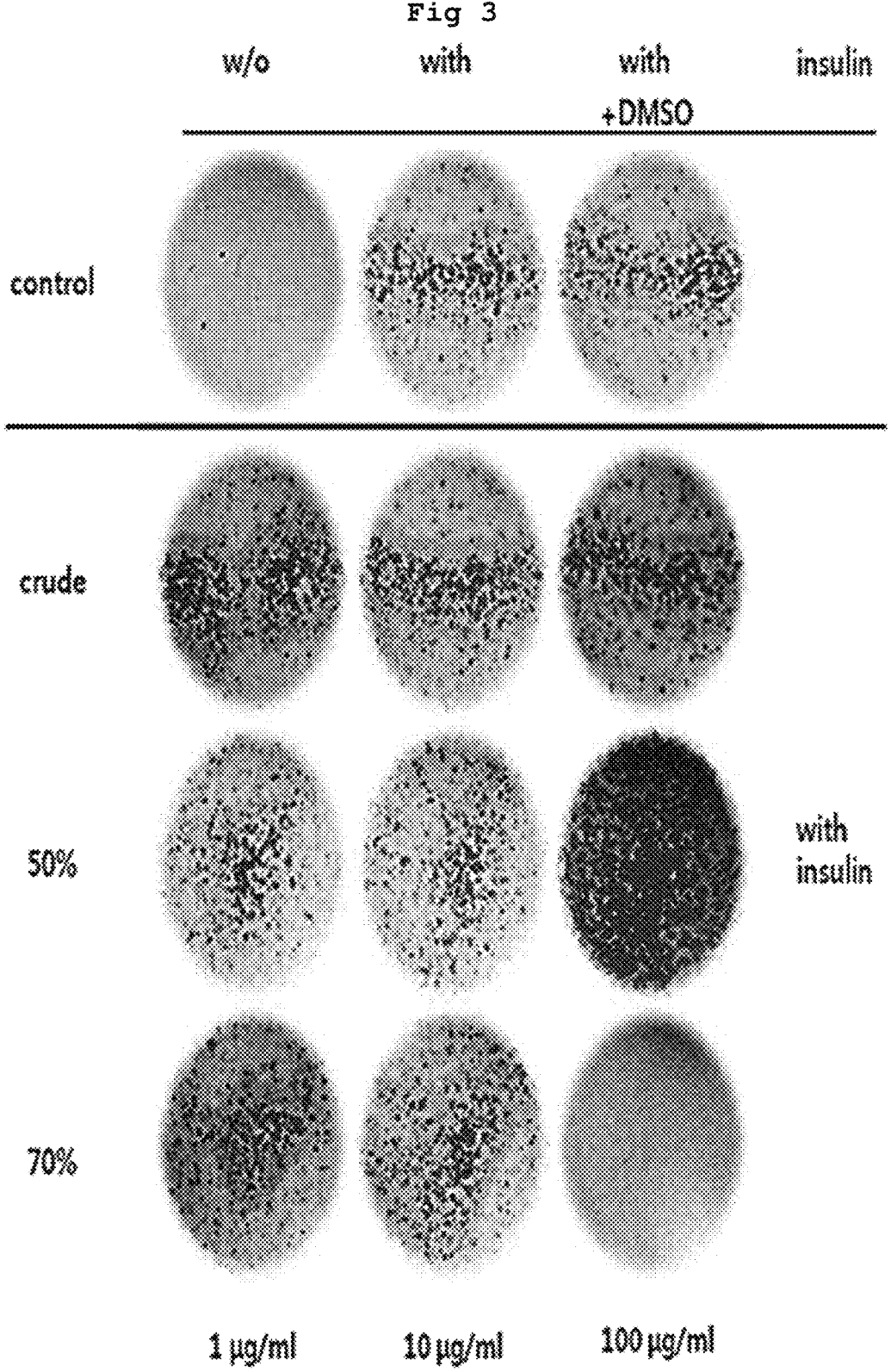
FIG. 3 is a diagram illustrating the accumulation of fat generated through glucose metabolism of adipocytes by the ethylacetate-methanol fraction of centipede grass extract.

As a result, the fat accumulation in adipocytes of the group treated with 100 μg/ml of the ethylacetate-50% methanol fraction was approximately at least 300% increased, compared with the group treated with a low concentration of insulin. This result suggests that the ethylacetate-50% methanol fraction increased the inflow of glucose in adipocytes (FIG. 2 and FIG. 3).

Experimental Example 2: Hypoglycemic Effect of Centipede Grass Ethylacetate-Methanol Fraction on Test Animal The hypoglycemic activity of the centipede grass extract fraction was investigated with type II diabetic mice (db/db mice). C57BL/6 mice were used as the normal control group and C57BLKS/J-db/db mice were used as the diabetes induced mouse group. Both animals were purchased from SLC Co., JAPAN, via Central Lab Animal Inc., and at the time of purchase, the animals were 7 weeks old. After arrived at the animal lab, the animals were adapted for a week at the temperature of 22° C. with the humidity of 50%. When they were 9 weeks old or older, blood was collected from the tail and blood glucose was measured. Diabetic activity test was performed from when they were 14 weeks old or older when the blood glucose level of the animal reached 350 mg/dL. The mice displaying the blood glucose higher than the standard (350 mg/dL) were randomly mixed in every group. The normal control group and the diabetes induced group were orally administered with corn oil alone every day, while the rest of the experimental groups were orally administered with the sample prepared suitable for each group and the sample mixed in corn oil every day. The dose for the oral administration was 200~300 µl/mouse. The reagent and sample were administered for 10 days consecutively and then the sample administration was stopped for 2 days, during which the changes of blood glucose were examined. The sample administration was started again and the changes of blood glucose were observed.

Figure 4:
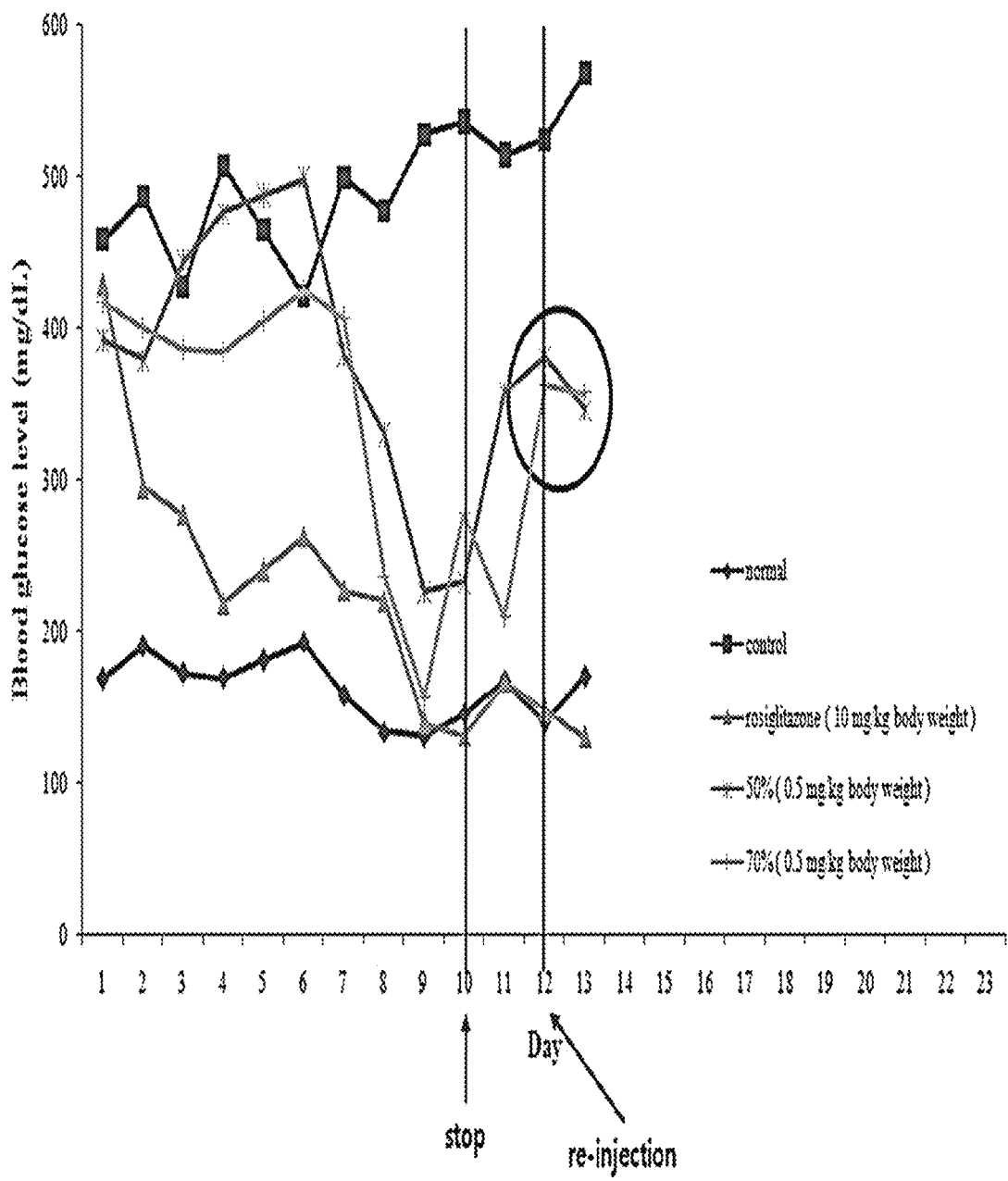
FIG. 4 is a diagram illustrating the hypoglycemic activity of the ethylacetate-methanol fraction of centipede grass extract confirmed in type II diabetic mice.

As a result, the level of blood glucose of the group treated with the centipede grass ethylacetate-50% fraction or 70% methanol fraction for 10 days was lowered 70~80%, compared with that of the diabetes induced group. When the sample administration was stopped, the mouse blood glucose level rose again, suggesting that the ethylacetate-50% methanol fraction and the ethylacetate-70% methanol fraction could reduce the blood glucose level (FIG. 4).

Experimental Example 3: Oral Glucose Tolerance Test (OGTT) with Centipede Grass Ethylacetate-Methanol Fraction Oral glucose tolerance test is one of the methods for diagnosing diabetes that has been most widely used nowadays, in which glucose is orally administered on fasting condition and then blood glucose is measured. The animals used for this test were purchased from SLC Co., JAPAN, via Central Lab Animal Inc., which were C57BLKS/J-db/db mice. The animals proceeded to anti-diabetes test by using the centipede grass ethylacetate-methanol fraction for 2 weeks. After two weeks of test, the animals proceeded to adaptation for 2 weeks. Then, the animals were used for OGTT. Particularly, the mice were fasted for 18 hours to maintain empty stomach. 30 minutes before the glucose administration, the sample (50% or 70% fraction; 10 mg/kg of weight) was mixed in corn oil, which was orally administered to the mice. Glucose was orally administered at the concentration of 2 g/kg of body weight. Then the changes of blood glucose were observed at 30 minutes intervals for 6 times total.

Figure 5:
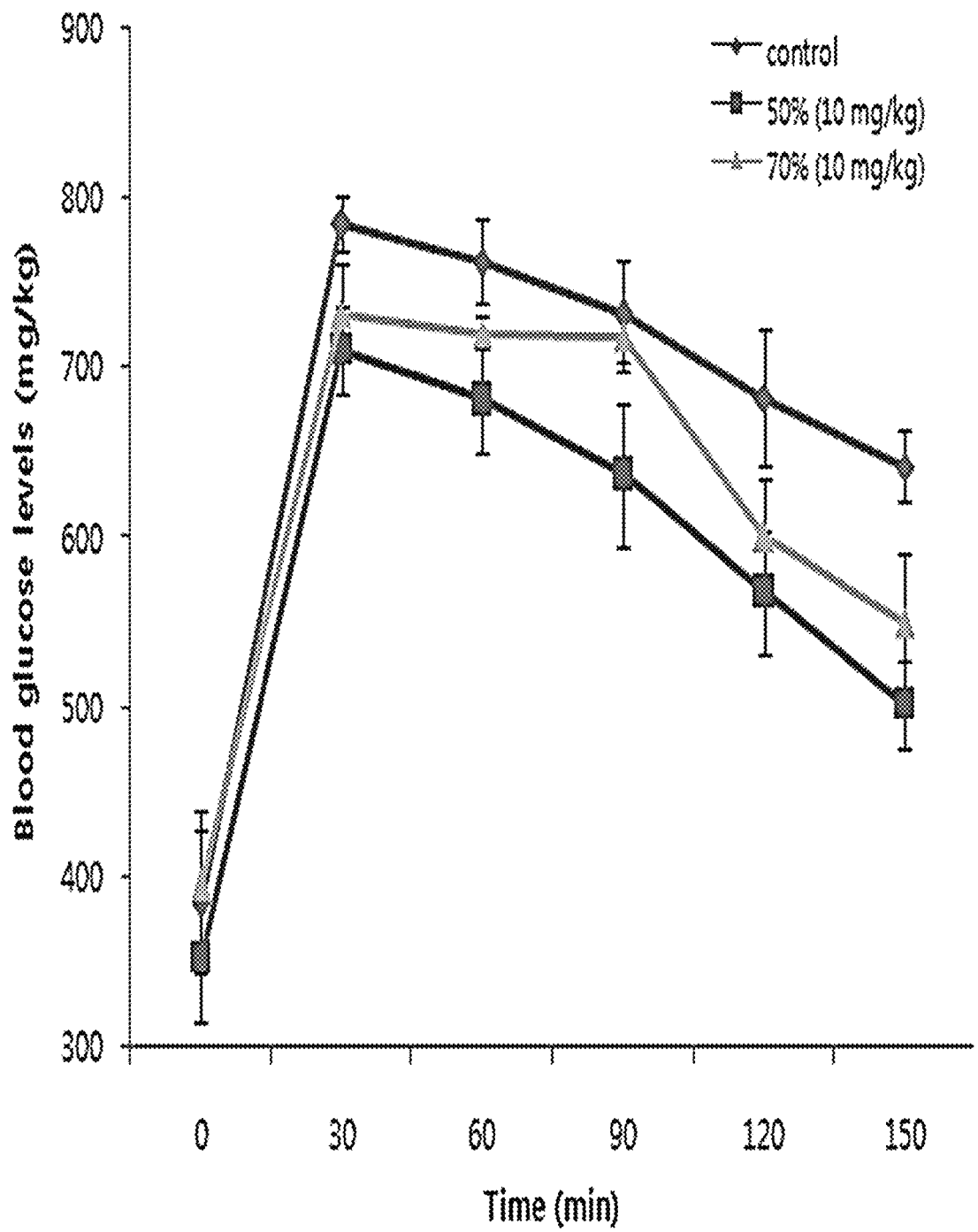
FIG. 5 is a diagram illustrating the anti-diabetic activity of the centipede grass ethylacetate-methanol fraction confirmed in type II diabetic mice.
Figure 6:
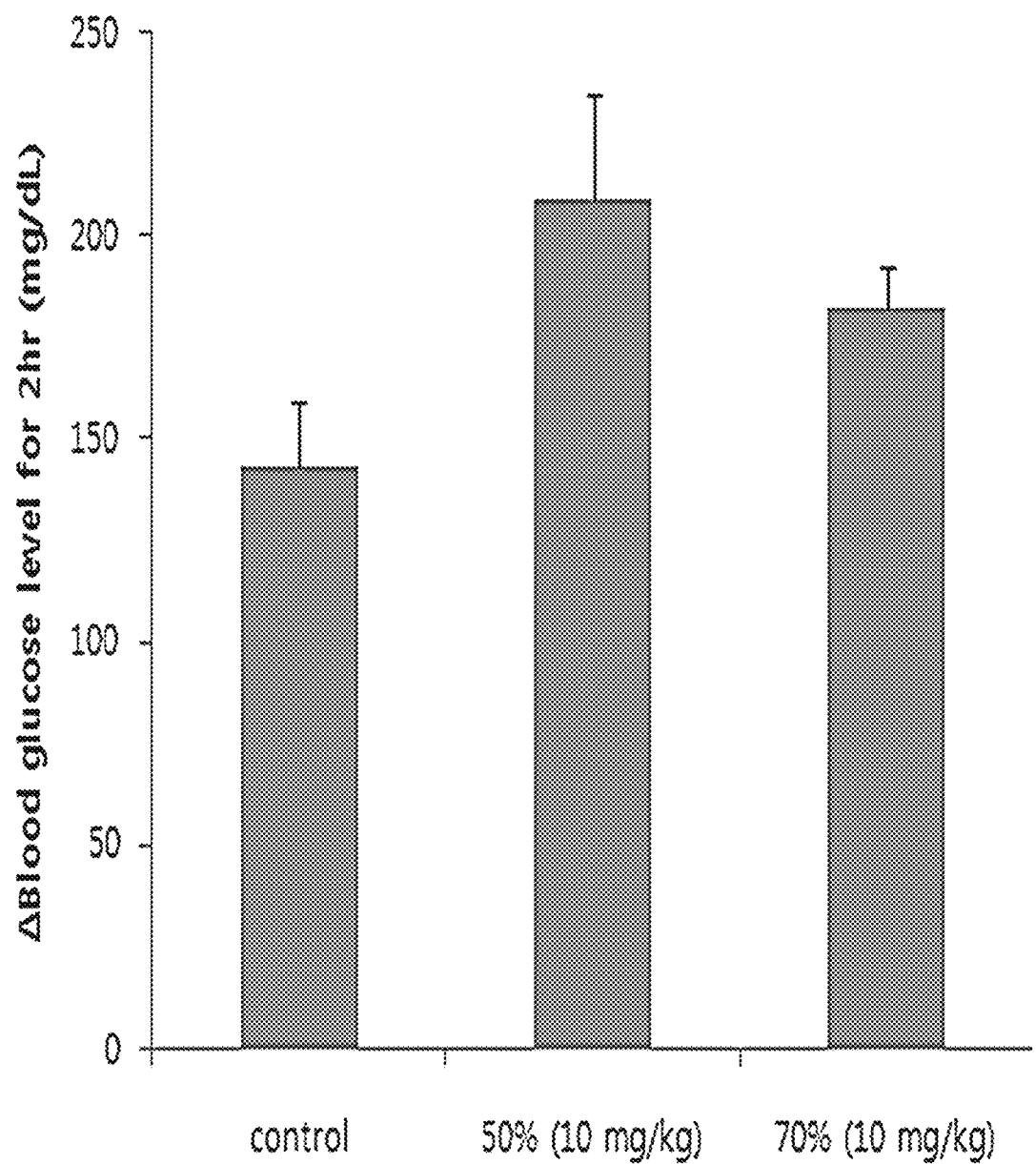
FIG. 6 is a diagram illustrating the changes of blood glucose level in type II diabetic mice confirmed by oral glucose tolerance test.

As a result, the rapid increase of blood glucose expected after the glucose administration was suppressed approximately 25% in the mouse group treated with the centipede grass ethylacetate-methanol fraction, compared with the comparative control group. 150 minutes later, the blood glucose lowering effect was increased at the level of 60% by that of the comparative control group. The results indicate that the centipede grass ethylacetate-methanol fraction could regulate blood glucose (FIG. 5 and FIG. 6).

Experimental Example 4: Oral Glucose Tolerance Test (OGTT) with Centipede Grass Ethylacetate-Methanol Fraction at Different Concentrations C57BL/6 mice were used as the normal control group and C57BLKS/J-db/db mice were used as the diabetes induced mouse group. Both animals were purchased from SLC Co., JAPAN, via Central Lab Animal Inc., and at the time of purchase, the animals were 7 weeks old. After arrived at the animal lab, the animals were adapted for a week at the temperature of 22° C. with the humidity of 50%. Before the test, the animals were fasted for 12 hours to maintain empty stomach. 30 minutes before the glucose administration, the sample (crude or 50% or 70% fraction; 1 mg/kg or 10 mg/kg of body weight) was mixed in corn oil, which was orally administered to the mice. Glucose was orally administered at the concentration of 2 g/kg of body weight. Then the changes of blood glucose were observed at 30 minutes intervals for 6 times total.

Figure 7:
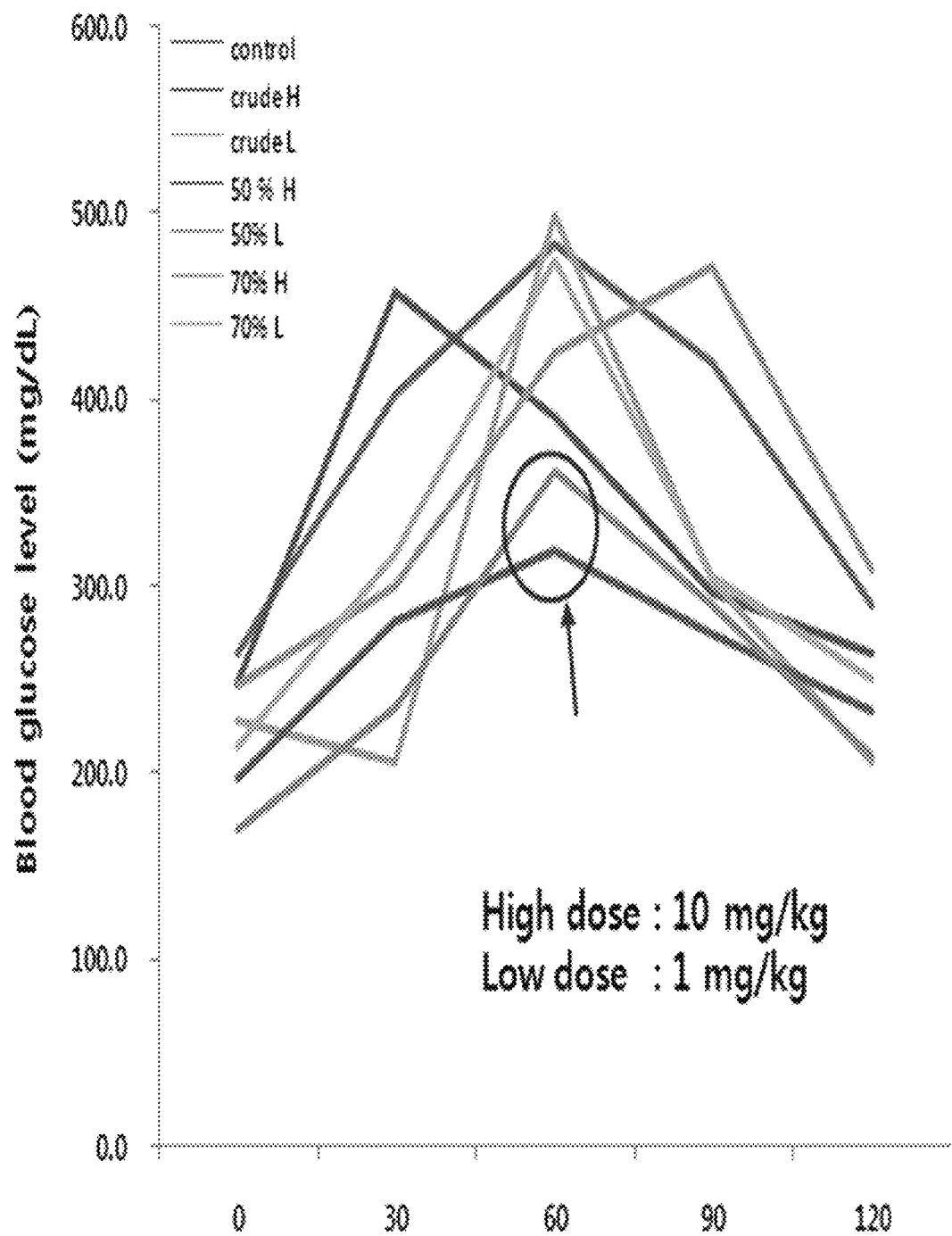
FIG. 7 is a diagram illustrating the results of oral glucose tolerance test with the centipede grass ethylacetate-methanol fraction at the concentrations of 1 mg/kg and 10 mg/kg.

As a result, the rapid increase of blood glucose expected after the glucose administration was suppressed to the level of 40% and 60% by the comparative control group respectively by a high dose and a low dose of the centipede grass ethylacetate-50% methanol fraction 60 minutes after the treatment (FIG. 7).

Experimental Example 5: Intraperitoneal Glucose Tolerance Test (IPGTT) with Centipede Grass Ethylacetate-Methanol Fraction at Different Concentrations C57BL/6 mice were used as the normal control group and C57BLKS/J-db/db mice were used as the diabetes induced mouse group. Both animals were purchased from SLC Co., JAPAN, via Central Lab Animal Inc., and at the time of purchase, the animals were 7 weeks old. After arrived at the animal lab, the animals were adapted for a week at the temperature of 22° C. with the humidity of 50%. Before the test, the animals were fasted for 12 hours to maintain empty stomach. 30 minutes before the glucose administration, the sample (crude or 50% or 70% fraction; 1 mg/kg or 10 mg/kg of body weight) was dissolved in 10 mM KOH, which was orally administered to the mice. Glucose was orally administered at the concentration of 2 g/kg of body weight. Then the changes of blood glucose were observed at 30 minutes intervals for 6 times total.

Figure 8:
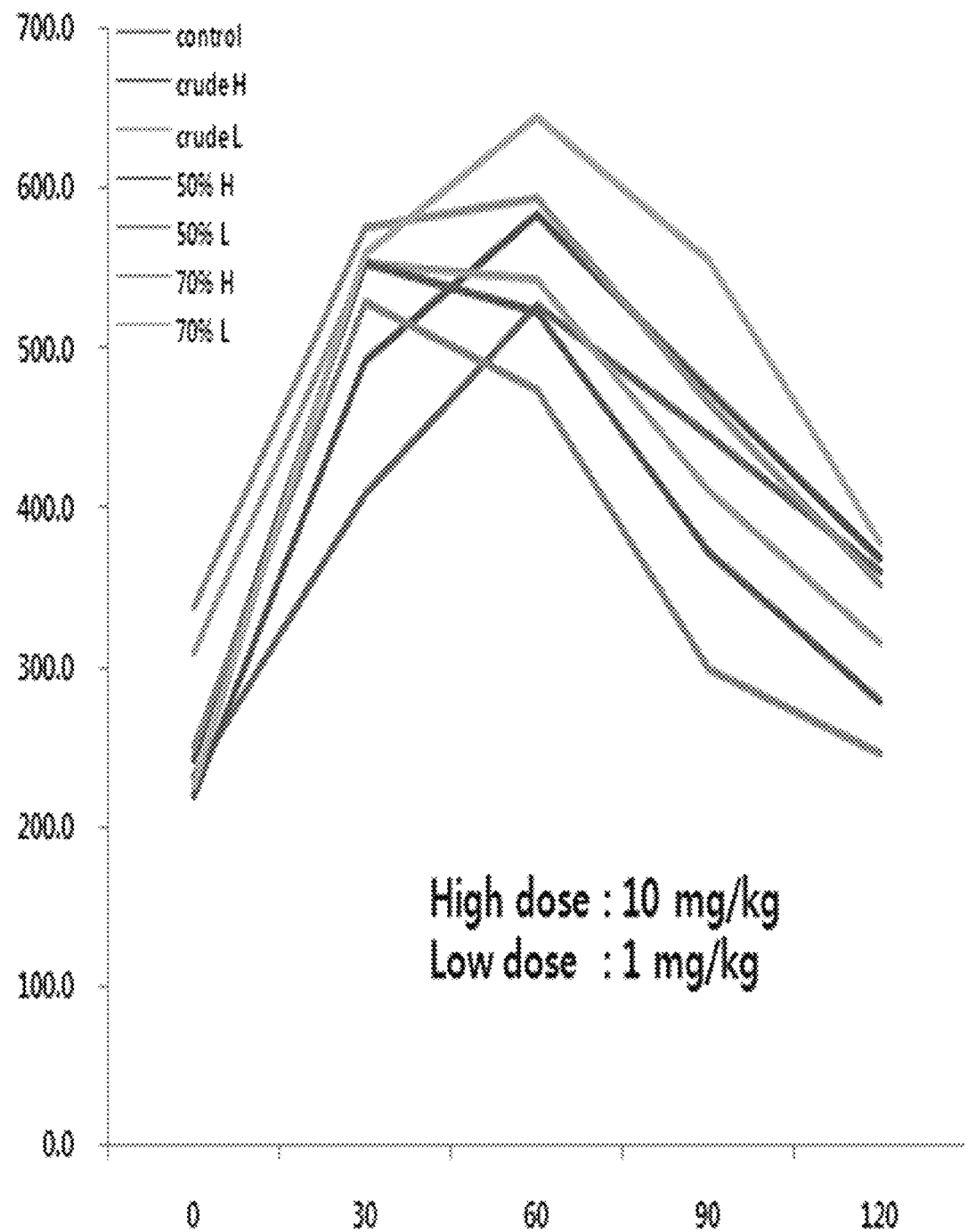
FIG. 8 is a diagram illustrating the results of intraperitoneal glucose tolerance test with the centipede grass ethylacetate-methanol fraction at the concentrations of 1 mg/kg and 10 mg/kg.

As a result, the blood glucose lowering effect was increased approximately 80% by that of the Comparative Control group 2 hours after the treatment of the centipede grass ethylacetate-50% methanol fraction at a high dose and a low dose (FIG. 8).

Experimental Example 6: Oral Glucose Tolerance Test (OGTT) with Centipede Grass Ethylacetate-Methanol Fraction According to Intraperitoneal Administration C57BLKS/J-db/db mice were used as the diabetes induced mouse group. The animals were purchased from SLC Co., JAPAN, via Central Lab Animal Inc., and at the time of purchase, the animals were 7 weeks old. After arrived at the animal lab, the animals were adapted for a week at the temperature of 22° C. with the humidity of 50%. Before the test, the animals were fasted for 12 hours to maintain empty stomach. 30 minutes before the glucose administration, the sample (crude or 50% or 70% fraction;

1 mg/kg or 10 mg/kg of body weight) was dissolved in 10 mM KOH, which was intraperitoneally administered to the mice. Glucose was orally administered at the concentration of 2 g/kg of body weight. At that time, the total amount for the administration was 200 μl respectively. Then, blood glucose was measured 9 times in 5 hours.

Figure 9:
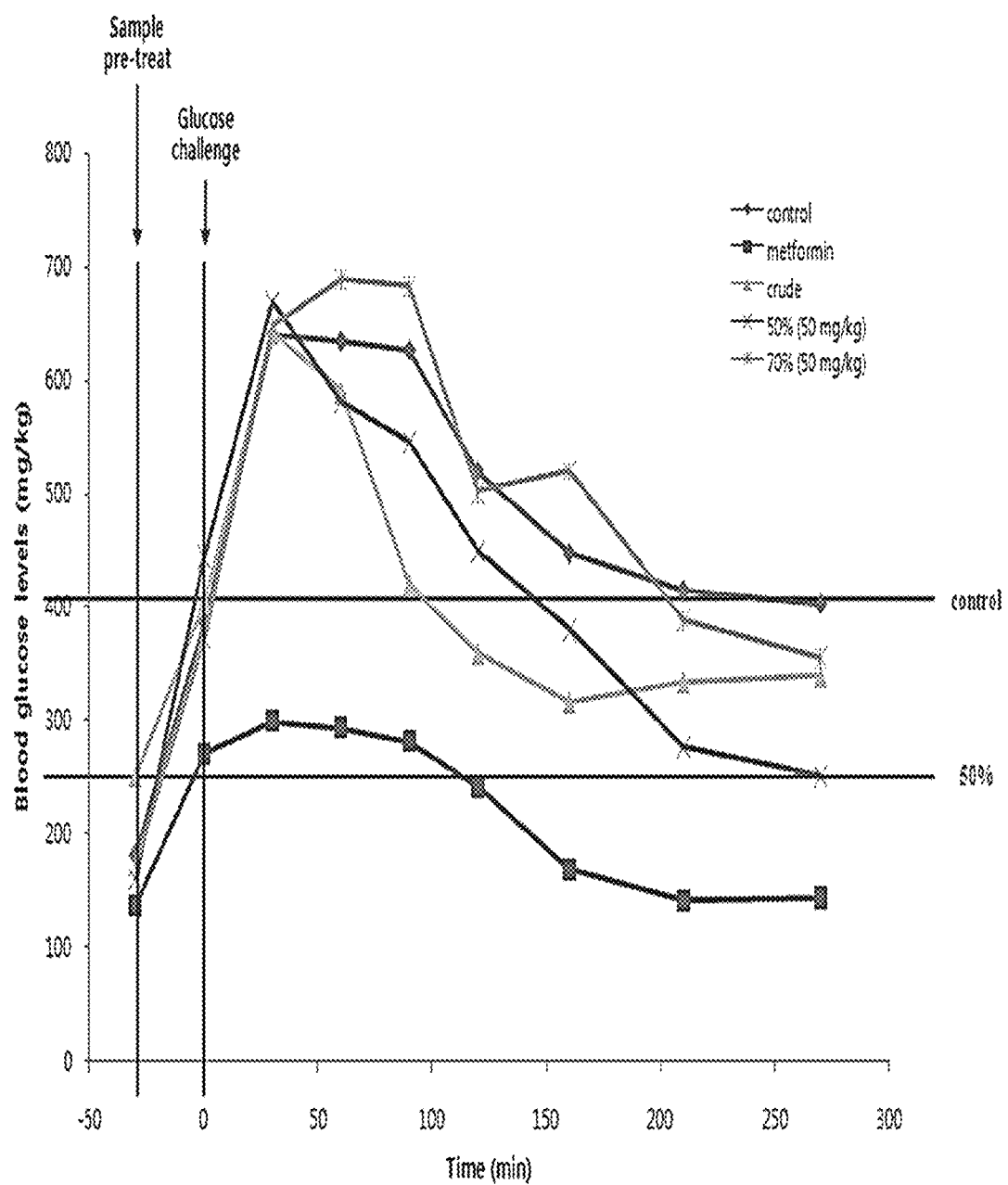
FIG. 9 is a diagram illustrating the changes of blood glucose confirmed by glucose oral glucose tolerance test performed after the intraperitoneal administration of the centipede grass ethylacetate-methanol fraction.

As a result, the level of blood glucose of the control group was maintained at 400 mg/dL or up 4.5 hours later, while the level of blood glucose of the group treated with the centipede ethylacetate-50% methanol fraction was lowered to 250 mg/dL, indicating that the blood glucose lowering effect was approximately 60% increased, compared with that of the control group (FIG. 9).

Experimental Example 7: Anti-Diabetic Activity of Centipede Grass Ethylacetate-Methanol Fraction in Streptozotocin (STZ)-Type I Diabetes Model The anti-diabetic activity of the centipede grass extracts was investigated using the diabetes induced ICR mice, precisely the streptozotocin (STZ)-type I diabetes induced model. The animals were purchased from SLC Co., JAPAN, via Central Lab Animal Inc., and at the time of purchase, the animals were 7 weeks old. After arrived at the animal lab, the animals were adapted for a week at the temperature of 22° C. with the humidity of 50%. To induce type I diabetes in the animal, β cells in the pancreas were selectively destroyed by using STZ to reduce insulin secretion. STZ was dissolved in 50 mM citrate buffer (pH 4.5), which was intraperitoneally injected to induce type I diabetes. The dose for the administration was 80 mg/kg of body weight, which was administered three times total at 2 days intervals. 3 days later, blood glucose was measured. The mice displaying the blood glucose level of 350 mg/dL or higher were selected and randomly distributed to the groups for the test. Before the best began, the animals were fasted for 12 hours to maintain empty stomach. 30 minutes before the glucose administration, the sample (50% or 70% fraction; 20 mg/kg of body weight) was mixed in corn oil, which was orally administered to the mice. Glucose was orally administered at the concentration of 2 g/kg of body weight. Blood glucose was measured total 10 times in 6 hours.

Figure 10:
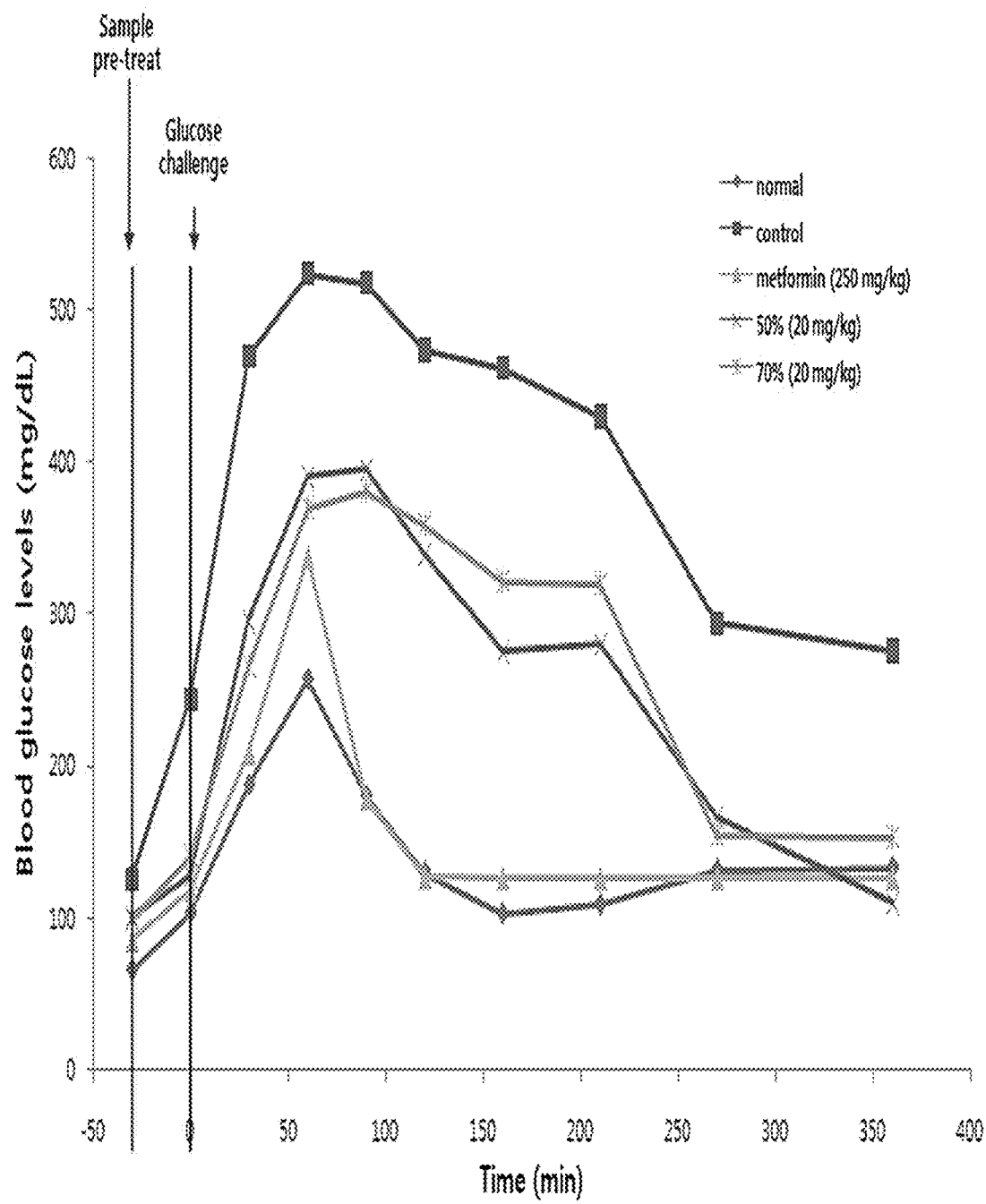
FIG. 10 is a diagram illustrating the changes of blood glucose in streptozotocin (STZ)-induced type I diabetic model, confirmed by oral glucose tolerance test performed to investigate the anti-diabetic activity of the centipede grass ethylacetate-methanol fraction.

As a result, the blood glucose level of the group treated with the centipede grass ethylacetate-methanol fraction was dropped to the normal level 4.5 hours later. However, the blood glucose level of the control group was still high, precisely 150 mg/dL higher than that of the normal group even after 6 hours. The group treated with the centipede grass ethylacetate-methanol fraction 6 hours after the glucose administration displayed the blood glucose lowering effect 100% by that of the control group (FIG. 10).

Experimental Example 8: Inhibition of Aβ(1-42) Peptide Oligo-Polymerization by Centipede Grass Extract or Fractions Thereof To investigate whether or not the centipede grass extract or the fractions thereof could inhibit the oligo-polymerization of Aβ(1-42) peptide, the recombinant Aβ peptide (Sigma) was dissolved in 1 mM hexafluoroisopropanol, which was then distributed in the sterilized microcentrifuge tube. After eliminating hexafluoroisopropanol in Speed Vac, the peptide was dissolved in 5 mM DMSO. The peptide was dissolved in 100 μM Ham's F-12 (final conc.), followed by reaction at 4° C. for 24 hours. 24 hours later, 300 μg of each centipede grass extract was added to the Aβ peptide sample, followed by reaction for 30 minutes. The Aβ oligo-polymerization was investigated by Western blotting.

Figure 11:
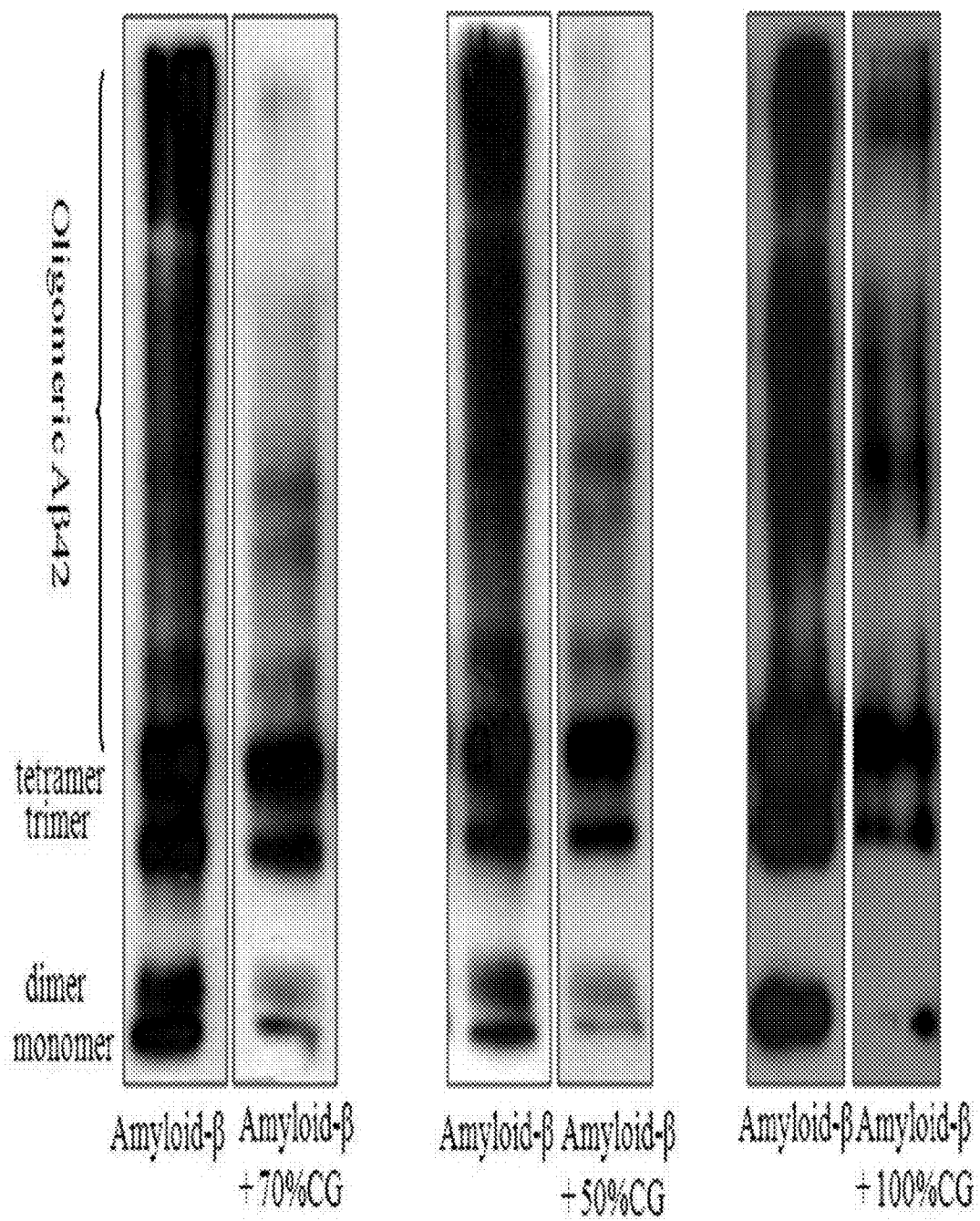
FIG. 11 is a diagram illustrating the inhibition of oligopolymerization of amyloid-beta peptide (Aβ1-42) by the centipede grass ethylacetate-methanol fraction.

As a result, the Aβ peptide was aggregated by the formation of Aβ peptide monomers, dimers, trimers, tetramers, and fibril forms in the control group not-treated with the centipede grass extract. However, the oligo-polymerization of Aβ peptide was inhibited in the group treated with the centipede grass extract. Particularly, the oligo-polymerization was significantly inhibited in the group treated with the centipede grass ethylacetate-50% methanol and ethylacetate-70% methanol fractions. The inhibition of oligo-polymerization by the centipede grass extract could recover the neural death and the suppressed signaling pathway by Aβ peptide in dementia lesion (FIG. 11).

Experimental Example 9: Inhibition of Dementia-Inducing Enzyme Activity by Centipede Grass Ethylacetate-Methanol Fraction <9-1> Inhibition of BACE1 Activity by Centipede Grass Ethylacetate-Methanol Fraction Analysis of the inhibition of BACE1 activity by the centipede grass ethylacetate-methanol fraction was performed with BACE1 (β-Secretase) FRET assay kit (Panvera). Particularly, 10 ul BACE1 substrate was added to 10 ul centipede grass fraction (1 ug/ul), which was mixed with 10 ul BACE1 enzyme, followed by reaction at room temperature for 60 minutes. After adding 10 ul stop solution thereto, fluorescence was measured at 545 nm.

Figure 12:
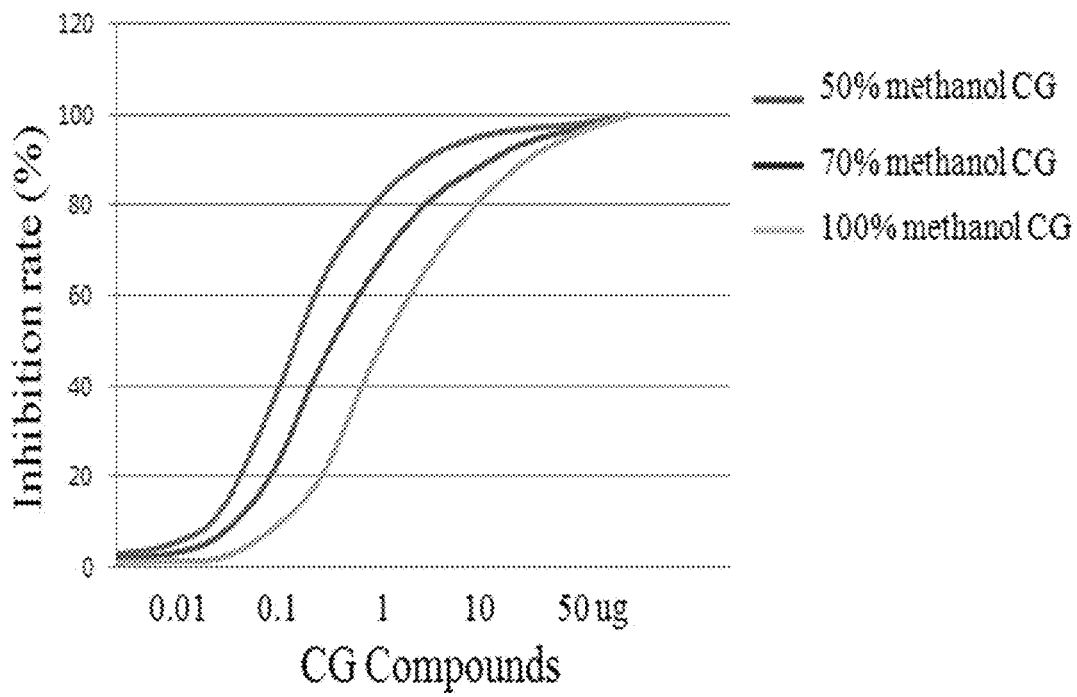
FIG. 12 is a diagram illustrating the inhibition of BACE1 activity by the centipede grass ethylacetate-methanol fraction.

As a result, the centipede grass ethylacetate-50% methanol fraction, centipede grass ethylacetate-70% methanol fraction, and centipede grass ethylacetate-100% methanol fraction were all confirmed to inhibit BACE1 activity in the reaction samples. Regarding the inhibition level, the centipede grass ethylacetate-50% methanol fraction demonstrated the strongest inhibition effect on BACE1, and the centipede grass ethylacetate-70% methanol and ethylacetate-100% methanol fractions followed in that order (FIG. 12).

<9-2> Inhibition of BACE1 Activity by Centipede Grass Ethylacetate-100% Methanol Fraction Analysis of the inhibition of BACE1 activity by the centipede grass ethylacetate-100% methanol fraction was performed with BACE1 (β-Secretase) FRET assay kit (Panvera). Particularly, 10 ul BACE1 substrate was mixed with 10 ul centipede grass fraction at different concentrations of 2 ug/ul, 0.75 ug/ul, and 0.2 ug/ul. 10 ul BACE1 enzyme was added thereto, followed by reaction at room temperature for 60 minutes. After adding 10 ul stop solution thereto, fluorescence was measured at 545 nm.

Figure 13:
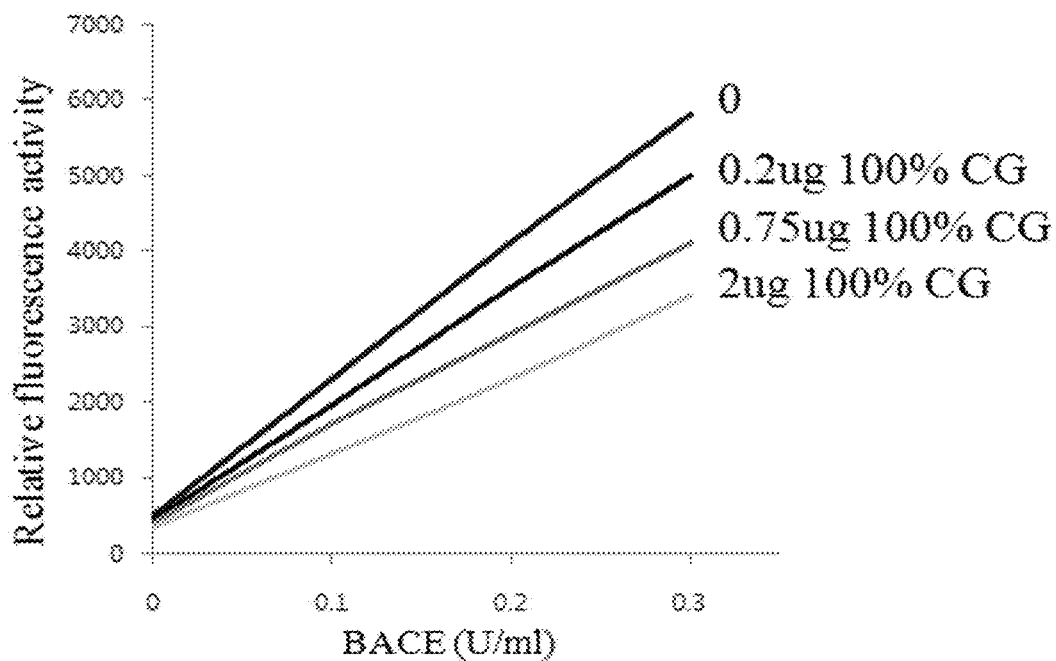
FIG. 13 is a diagram illustrating the inhibition of BACE1 activity by the centipede grass ethylacetate-100% methanol fraction dose-dependently.

As a result, all the centipede grass ethylacetate-100% methanol fractions were confirmed to inhibit BACE1 activity in the reaction samples. Regarding the inhibition level, 2 ug centipede grass ethylacetate-100% methanol fraction demonstrated the strongest inhibition effect on BACE1, and 0.75 ug centipede grass ethylacetate-100% methanol fraction and 0.2 ug centipede grass ethylacetate-100% methanol fraction followed in that order (FIG. 13).

<9-3> Inhibition of BACE1 Activity by Centipede Grass Ethylacetate-70% Methanol Fraction Analysis of the inhibition of BACE1 activity by the centipede grass ethylacetate-70% methanol fraction was performed with BACE1 (β-Secretase) FRET assay kit (Panvera). Particularly, 10 ul BACE1 substrate was mixed with 10 ul centipede grass fraction at different concentrations of 2 ug/ul, 0.75 ug/ul, and 0.2 ug/ul. 10 ul BACE1 enzyme was added thereto, followed by reaction at room temperature for 60 minutes. After adding 10 ul stop solution thereto, fluorescence was measured at 545 nm.

Figure 14:
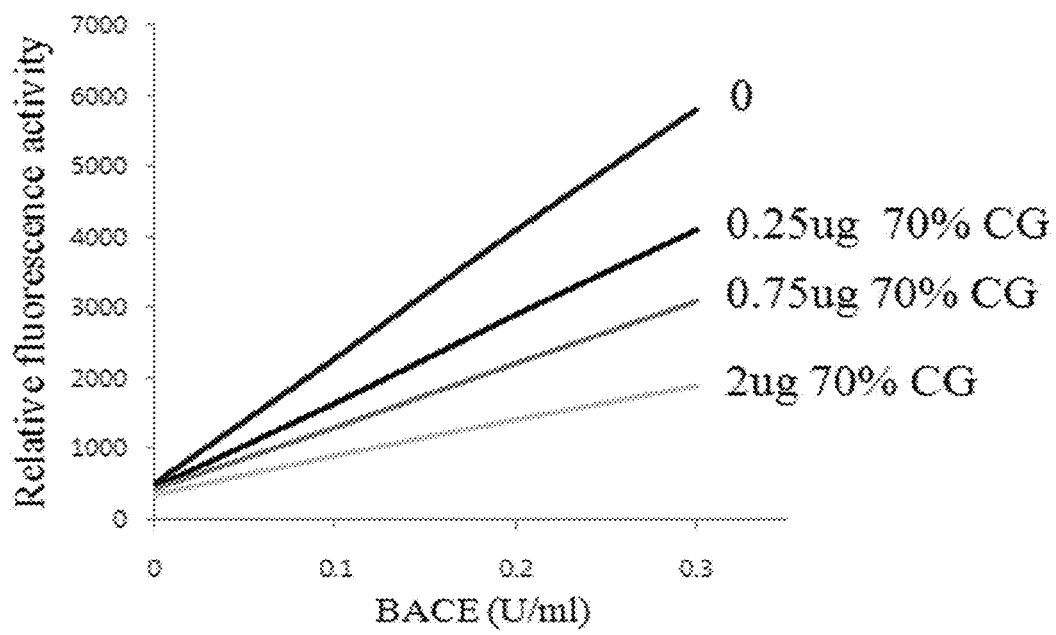
FIG. 14 is a diagram illustrating the inhibition of BACE1 activity by the centipede grass ethylacetate-70% methanol fraction dose-dependently.

As a result, all the centipede grass ethylacetate-70% methanol fractions were confirmed to inhibit BACE1 activity in the reaction samples. Regarding the inhibition level, 2 ug centipede grass ethylacetate-70% methanol fraction demonstrated the strongest inhibition effect on BACE1, and 0.75 ug centipede grass ethylacetate-70% methanol fraction and 0.2 ug centipede grass ethylacetate-70% methanol fraction followed in that order (FIG. 14).

<9-4> Inhibition of BACE1 Activity by Centipede Grass Ethylacetate-50% Methanol Fraction Analysis of the inhibition of BACE1 activity by the centipede grass ethylacetate-50% methanol fraction was performed with BACE1 (β-Secretase) FRET assay kit (Panvera). Particularly, 10 ul BACE1 substrate was mixed with 10 ul centipede grass fraction at different concentrations of 2 ug/ul, 0.75 ug/ul, and 0.2 ug/ul. 10 ul BACE1 enzyme was added thereto, followed by reaction at room temperature for 60 minutes. After adding 10 ul stop solution thereto, fluorescence was measured at 545 nm.

Figure 15:
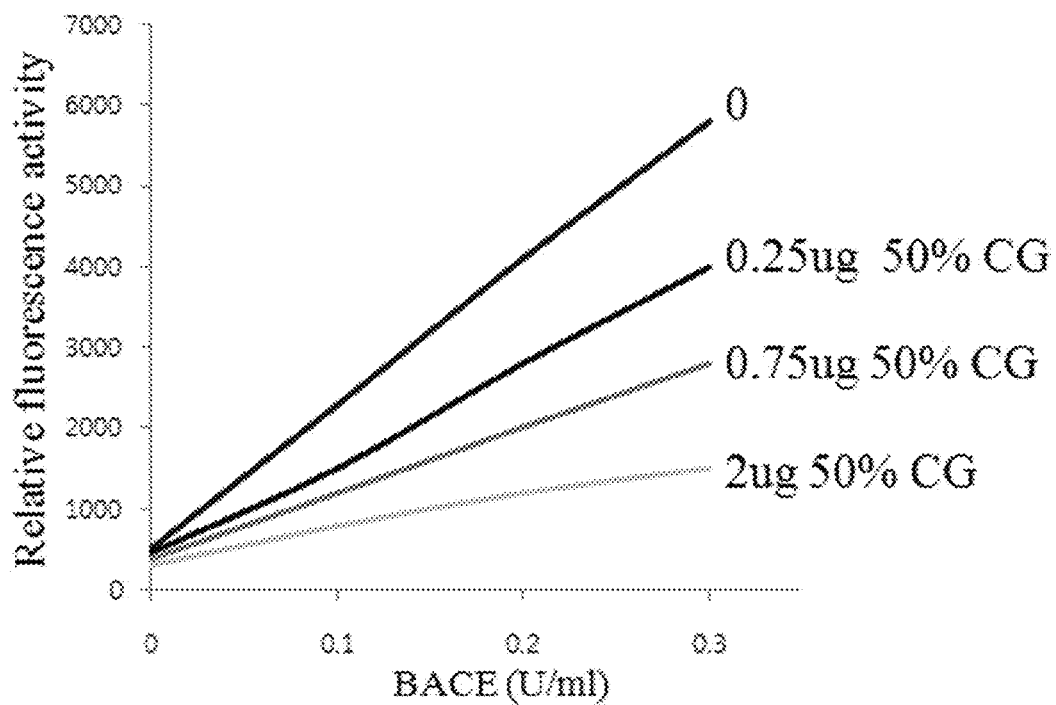
FIG. 15 is a diagram illustrating the inhibition of BACE1 activity by the centipede grass ethylacetate-50% methanol fraction dose-dependently.

As a result, all the centipede grass ethylacetate-50% methanol fractions were confirmed to inhibit BACE1 activity in the reaction samples. Regarding the inhibition level, 2 ug centipede grass ethylacetate-50% methanol fraction demonstrated the strongest inhibition effect on BACE1, and 0.75 ug centipede grass ethylacetate-50% methanol fraction and 0.2 ug centipede grass ethylacetate-50% methanol fraction followed in that order (FIG. 15).

Experimental Example 10: Inhibition of Dementia Inducing Enzyme Activity by Centipede Grass Ethylacetate-Methanol Fraction <10-1> Inhibition of Dementia Inducing Enzyme Activity by Centipede Grass Ethylacetate-70% Methanol Fraction Hippocampal HT-22 cells (American Type Culture Collection, ATCC) were treated with amyloid-beta oligomer, to which the centipede grass ethylacetate-70% methanol fraction was treated at different concentrations of 1, 25, 50, and 75 ug/ml. The oxidative stress increased ROS around mitochondria, causing apoptosis. Such oxidative stress-evoked mitochondrial damage causes the extracellular secretion of LDH, so the activity of LDH was measured.

Figure 16:
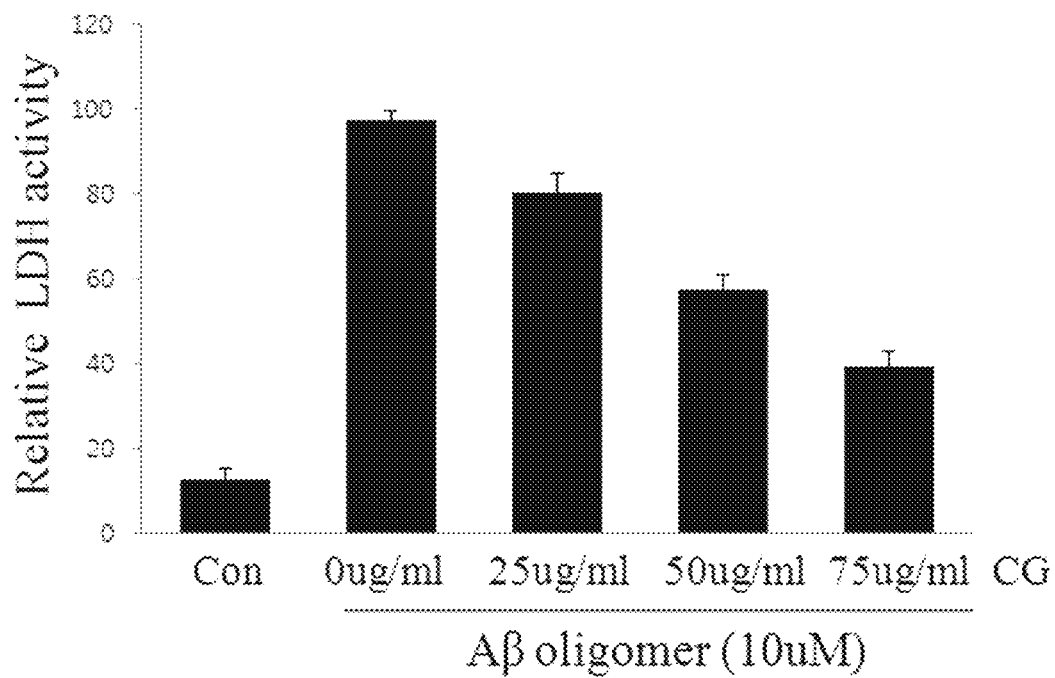
FIG. 16 is a diagram illustrating the inhibition of LDH activity by the centipede grass ethylacetate-70% methanol fraction dose-dependently.

As a result, the LDH activity in the normal group was approximately 16%, and the LDH activity in the control group treated with amyloid-beta oligomer was approximately 100%. In the meantime, the LDH activity in the group treated with the centipede grass ethylacetate-70% methanol fraction was reduced by the centipede grass extract dose-dependently, precisely the LDH activity was reduced to 81%, 63%, and 45% respectively by the centipede grass extract concentrations of 1, 25, 50, and 75 ug/ml. The above results indicate that the centipede grass ethylacetate-70% methanol fraction significantly inhibited cytotoxicity caused by amyloid-beta (FIG. 16).

<10-2> Inhibition of Dementia Inducing Enzyme Activity by Centipede Grass Ethylacetate-50% Methanol Fraction Hippocampal HT-22 cells (ATCC) were treated with amyloid-beta oligomer, to which the centipede grass ethylacetate-50% methanol fraction was treated at different concentrations of 1, 25, 50, and 75 ug/ml. The oxidative stress increased ROS around mitochondria, causing apoptosis. Such oxidative stress-evoked mitochondrial damage causes the extracellular secretion of LDH, so the activity of LDH was measured.

Figure 17:
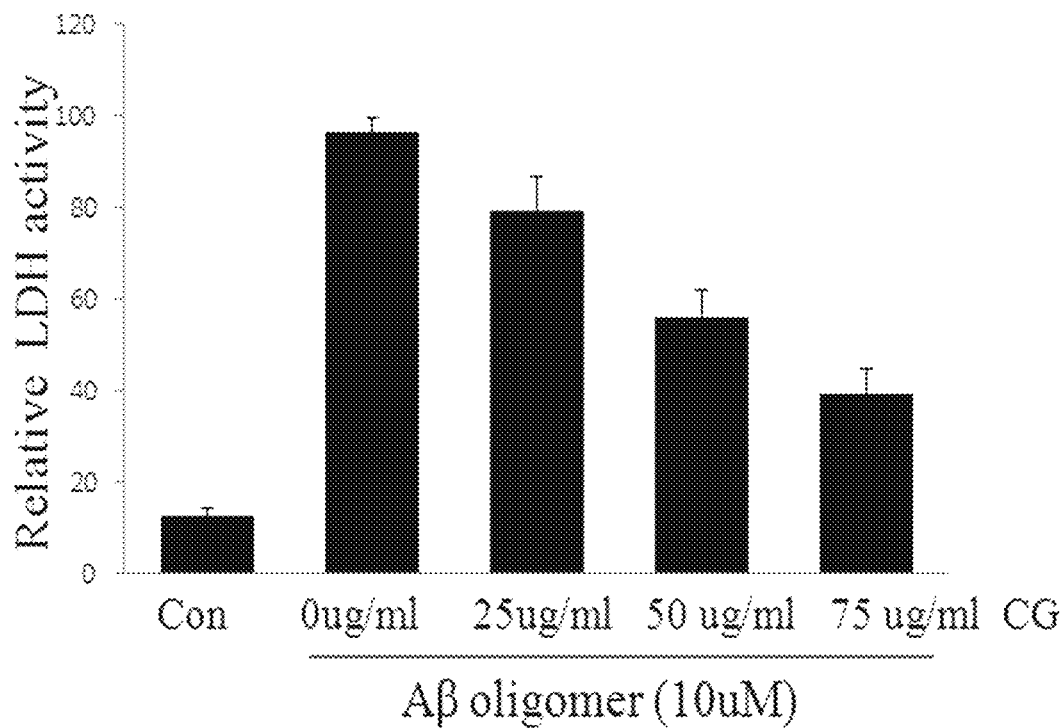
FIG. 17 is a diagram illustrating the inhibition of LDH activity by the centipede grass ethylacetate-50% methanol fraction dose-dependently.

As a result, the LDH activity in the normal group was approximately 17%, and the LDH activity in the control group treated with amyloid-beta oligomer was approximately 100%. In the meantime, the LDH activity in the group treated with the centipede grass ethylacetate-50% methanol fraction was reduced by the centipede grass extract dose-dependently, precisely the LDH activity was reduced to 79%, 57%, and 42% respectively by the centipede grass extract concentrations of 1, 25, 50, and 75 ug/ml. The above results indicate that the centipede grass ethylacetate-50% methanol fraction significantly inhibited cytotoxicity caused by amyloid-beta (FIG. 17).

<10-3> Inhibition of Dementia Inducing Reactive Oxygen Species (ROS) by Centipede Grass Ethylacetate-50% Methanol Fraction Hippocampal HT-22 cells (ATCC) were treated with amyloid-beta oligomer, to which the centipede grass ethylacetate-50% methanol fraction was treated at different concentrations of 1, 25, 50, and 75 ug/ml. The oxidative stress increased ROS around mitochondria, causing apoptosis. Such oxidative stress-evoked mitochondrial damage causes the extracellular secretion of LDH, so the activity of LDH was measured.

Figure 18:
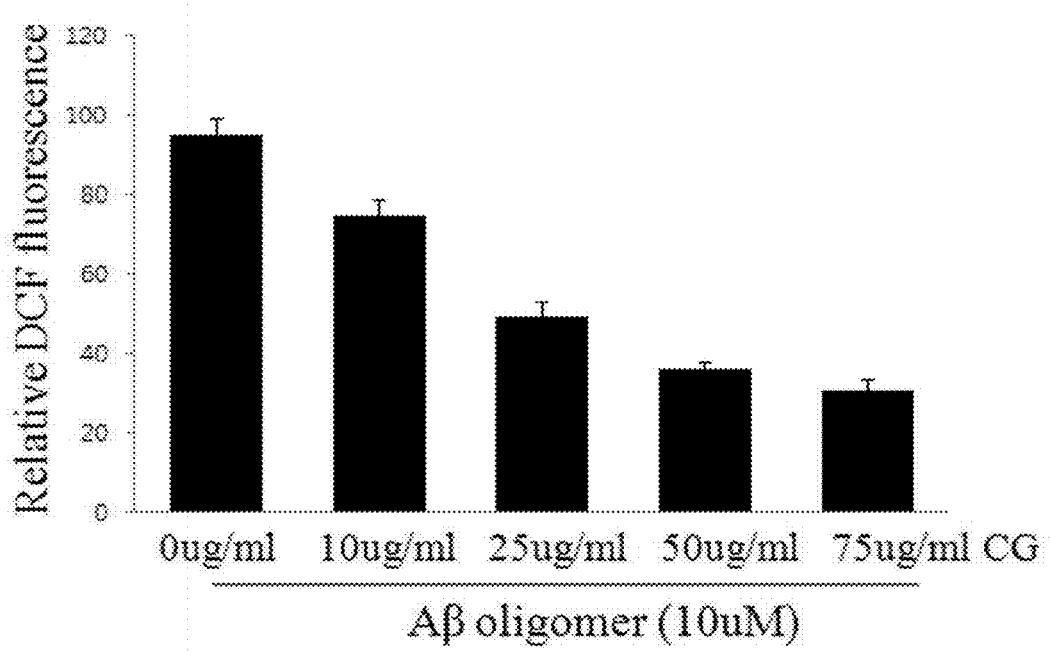
FIG. 18 is a diagram illustrating the inhibition of ROS production by the centipede grass ethylacetate-70% methanol fraction dose-dependently.

Particularly, hippocampal HT-22 cells were treated with amyloid-beta at the final concentration of 10 µM, followed by culture for overnight. Then, it was investigated whether or not the accompanied oxidative stress could increase ROS around mitochondria. DCF changes were quantified by using CytoFluor 40000 fluorescence spectrophotometer (TECAN infinite M200). As a result, ROS of the control group treated with amyloid-beta was quantified as 100%, and the groups treated with the centipede grass ethylacetate-70% methanol fraction at different concentrations of 10, 25, 50, and 75 ug/ml demonstrated ROS respectively 77%, 58%, 45%, 38%, and 36%. The above results indicate that the ethylacetate-50% methanol fraction significantly inhibited the ROS generation induced by amyloid-beta (FIG. 18).

Experimental Example 11: Inhibition of BACE1 Mediated Amyloid-Beta Secretion by Centipede Grass Ethylacetate-Methanol Fraction The effect of the centipede grass ethylacetate-methanol fraction on the amyloid-beta secretion in the cells over-expressing BACE1 (β-APP cleaving enzyme 1) that is an enzyme to produce dementia-inducing beta-amyloid and amyloid precursor protein (APP) was investigated.

Figure 19:
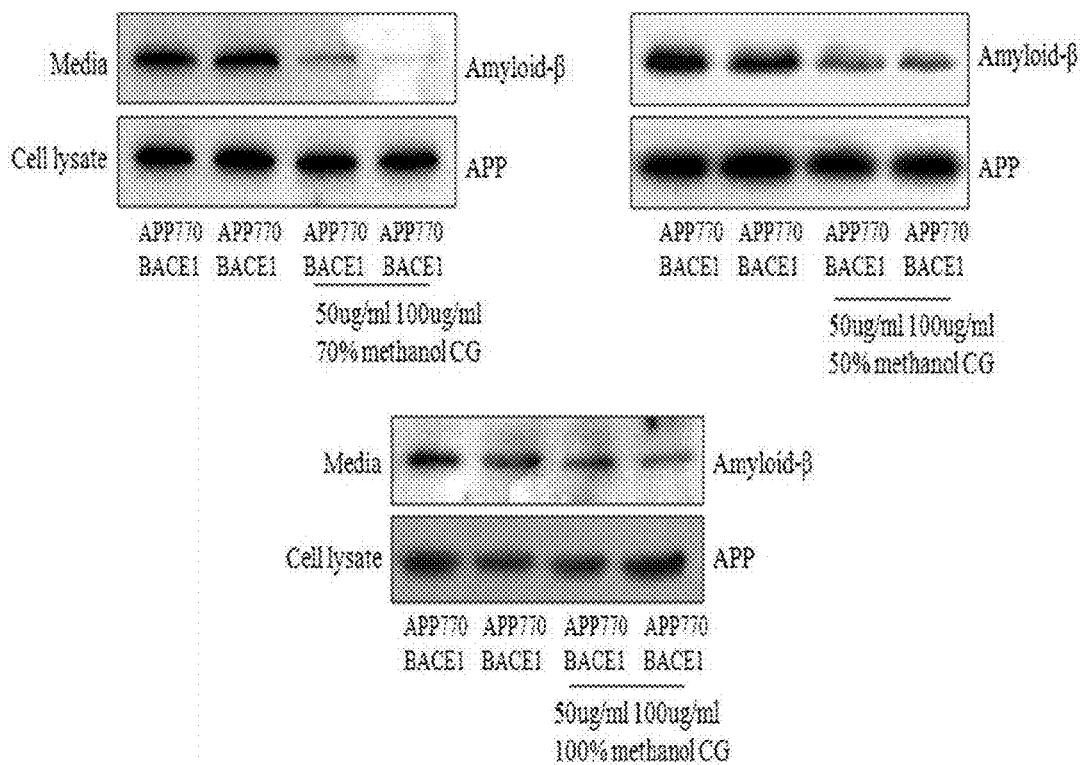
FIG. 19 is a diagram illustrating the inhibition of amyloid-beta secretion by the centipede grass ethylacetate-methanol fraction.

As a result, the amyloid-beta secretion was increased by the expression of BACE1, but the amount of amyloid-beta secreted in the medium treated with the centipede grass ethylacetate-50% methanol fraction or ethylacetate-70% methanol fraction was significantly reduced. Therefore, it was confirmed that the centipede grass ethylacetate-methanol fraction reduced amyloid-beta production by suppressing BACE1 activity (FIG. 19).

Experimental Example 12: Effect of Centipede Grass Ethylacetate-Methanol Fraction on Liver Toxicity The effect of the centipede grass ethylacetate-methanol fraction on the liver toxicity was investigated by treating the fraction to APP/PS1 mice (Central Lab Animal Inc.).

Particularly, the centipede grass ethylacetate-methanol fraction was treated to APP/PS1 mice, and then liver enzyme test was performed to measure aspartate aminotransferase (AST), alanine aminotransferase (ALT), and alkaline phosphatase (ALP).

Figure 20:
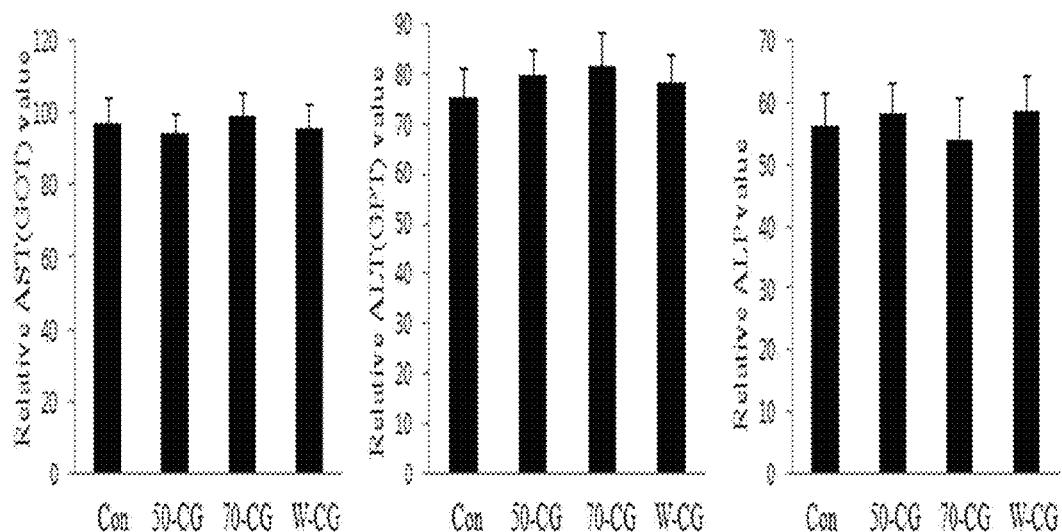
FIG. 20 is a diagram illustrating that the centipede grass ethylacetate-methanol fraction was not involved in liver toxicity.

As a result, the levels of AST, ALT, and ALP in the control APP mouse blood was not much different but as in the normal range as those of the experimental group treated with the centipede grass ethylacetate-methanol fraction, suggesting that the centipede grass ethylacetate-methanol fraction did not have liver toxicity (FIG. 20).

Experimental Example 13: Investigation of Cytokine Gene mRNA Expression According to the Treatment of Centipede Grass Ethylacetate-Methanol Fraction in the Test Animal To measure the expression of cytokine gene mRNA in APP mice (Sigma Co.) and in the mice treated with the centipede grass ethylacetate-methanol fraction, the expressions of mRNAs of IL-1a, IFN-g, and IL-6 expressed in the control APP mouse spleen were compared with those of the experimental group treated with the centipede grass ethylacetate-methanol fraction, for which RNA was extracted from each tissue and cDNA was synthesized from the RNA, followed by RT-PCR.

Particularly, to extract total RNA from spleen tissue, tissues were pulverized by using a homogenizer after adding Trizol solution (Invitrogen, USA) (1 ml/100 mg tissue). To separate protein and RNA layers, 200 μl of chloroform solution (Sigma Co.) was added to the above mixture, followed by vortexing vigorously. The mixture stood at room temperature for 3 minutes, followed by centrifugation at 12,000 rpm for 15 minutes. The colorless supernatant was transferred in a new tube by pippeting. Isopropanol (Sigma) was added to Trizol by 0.5 ml per 1 ml of Trizol, which stood at room temperature for 10 minutes. The mixture was centrifuged at 13,000 rpm for 15 minutes and then the supernatant was discarded and the precipitate was washed with 75% ethanol. After examining RNA concentration, cDNA was synthesized from the RNA by using 1 ug of total RNA as a template with oligo-dT primers and a reverse transcriptase. Target genes were IL-1α, INF-γ, and IL-6. For PCR with the control for quantification, β-actin primer was used. As primers, IL-1α (Sense-AGGAGAGCCGGGT-GACAGTA (SEQ. ID. NO: 1)) and (Antisense-AACTCA-GCCGTCTCTTCTTCAGA (SEQ. ID. NO: 2)), IFN-γ (Sence-TGAACGCTACACACTGCATCTTG (SEQ. ID. NO: 3) and (Antisense-GTTATTCAGACTTTCTAG-GCTTTCAATG (SEQ. ID. NO: 4)), and IL-6 (Sence-GAG-GATACCACTCCCAACAGACC (SEQ. ID. NO: 5)) and (Antisense-AAGTGCATCATCGTTGTTCATACA (SEQ. ID. NO: 6)) were used. The synthesized cDNA, primers, dNTP mixture (2.5 mM), Ex-tag polymerase (Takara), and PCR buffer were all mixed and PCR was performed as follows: denaturation at 94° C. for 30 seconds, annealing at 55° C. for 40 seconds, and extension at 72° C. for 50 seconds.

Figure 21:
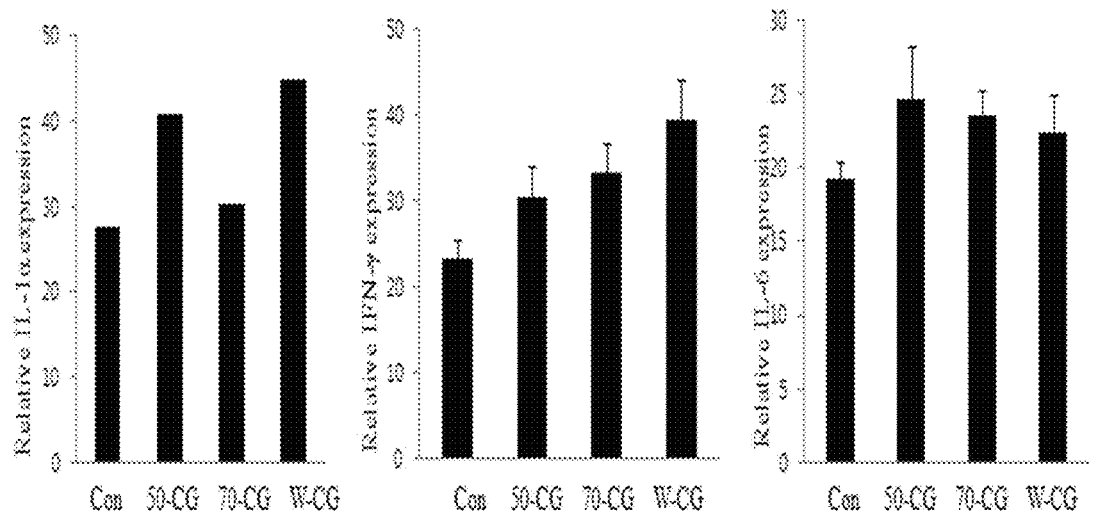
FIG. 21 is a diagram illustrating the expression of cytokinin mRNA in the spleen of APP/PS1 mice treated with the centipede grass ethylacetate-methanol fraction.

As a result, the expressions of mRNAs of IL-1α, IFN-g, and IL-6 were high in the spleen of the mouse treated with the centipede grass ethylacetate-50% methanol, ethylacetate-70% methanol, or ethylacetate-100% methanol extract, compared with the control APP mouse (FIG. 21).

Experimental Example 14: Expressions of Immunoglobulin, Cytokine, INF-1β, IFN-γ, and Amyloid-Beta in the Test Animal According to the Treatment of Centipede Grass Ethylacetate-Methanol Fraction ELISA (enzyme-linked immunosorbent assay, Diagnostic Automation/Cortez Diagnostics, INC.) was performed to examine immune activity, cytokine activity, and the levels of INF-1β, IFN-γ, and amyloid-beta (Aβ) in the blood of both the control APP mice and the mice treated with the centipede grass ethylacetate-methanol fraction.

Particularly, asepromazine (Sigma Co.) and ketamine (Sigma Co.) were mixed to prepare anesthesia liquid, which was administered to the test mouse (B6C3-Tg (APPswe, PSEN1dE9) 85Dbo/Mmjax, The Jackson Laboratory) via intramuscular injection. Then, blood was taken from the heart, which was transferred in a heparin tube. The tube was centrifuged at 1000 rpm for 10 minutes to separate serum. ELISA was performed using each cytokine assay kit (Enzo). The sample blood was loaded on the antibody conjugated plate, followed by reaction in a plate shaker for 1~2 hours. After washing the plate 4~5 times to eliminate the non-specific reaction product, each antibody matched to the sample was added, followed by reaction for 1 hour. After washing again the plate 4~5 times, HRP conjugate was added, leading to the secondary antibody conjugation for 1 hour. After washing thereof 4~5 times, substrate was added thereto to induce enzyme reaction. When an antigen was there, the reaction mixture became blue. The color development was terminated by adding a stop solution. When the color turned to yellow, $OD_{450}$ was measured.

Figure 22:
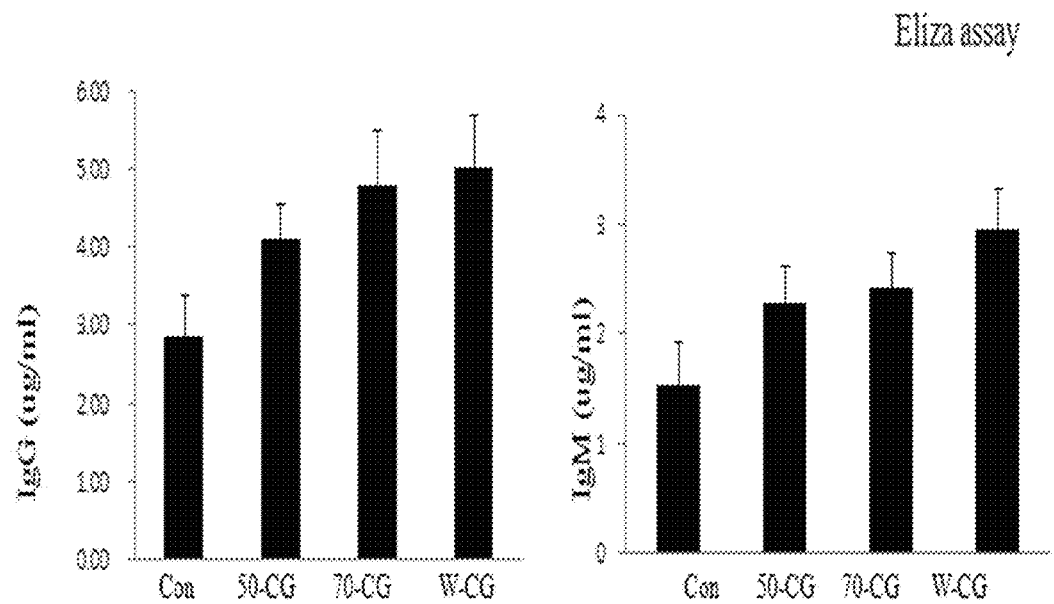
FIG. 22 is a diagram illustrating the expression of immunoglobulin in APP/PS1 mice treated with the centipede grass ethylacetate-methanol fraction.

As a result, the immunoglobulin activity was high in the groups treated with the centipede grass ethylacetate-50% methanol fraction, the centipede grass ethylacetate-70% methanol fraction, and the centipede grass ethylacetate-100% methanol fraction, compared with that of the control. The immune activity was also high in those groups treated with the centipede grass ethylacetate-methanol fractions, compared with that of the control group (FIG. 22).

Figure 23:
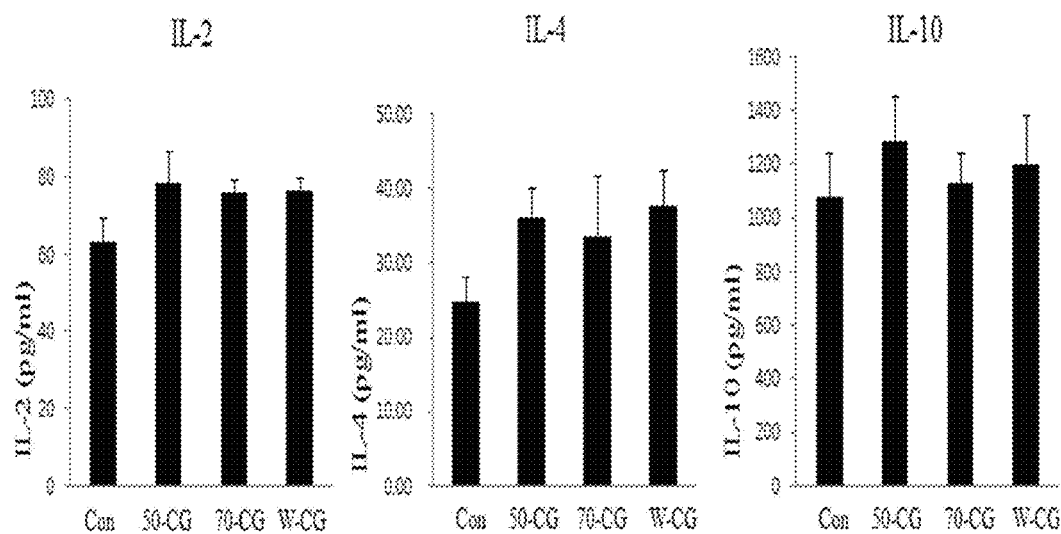
FIG. 23 is a diagram illustrating the expression of immunoglobulin (IgG and IgM) in APP/PS1 mice treated with the centipede grass ethylacetate-methanol fraction.

The cytokine level was also high in the groups treated with the centipede grass ethylacetate-50% methanol fraction, the centipede grass ethylacetate-70% methanol fraction, and the centipede grass ethylacetate-100% methanol fraction, compared with that of the control. This result also supported that the immune activity was high in the groups treated with the centipede grass ethylacetate-methanol fractions (FIG. 23).

Figure 24:
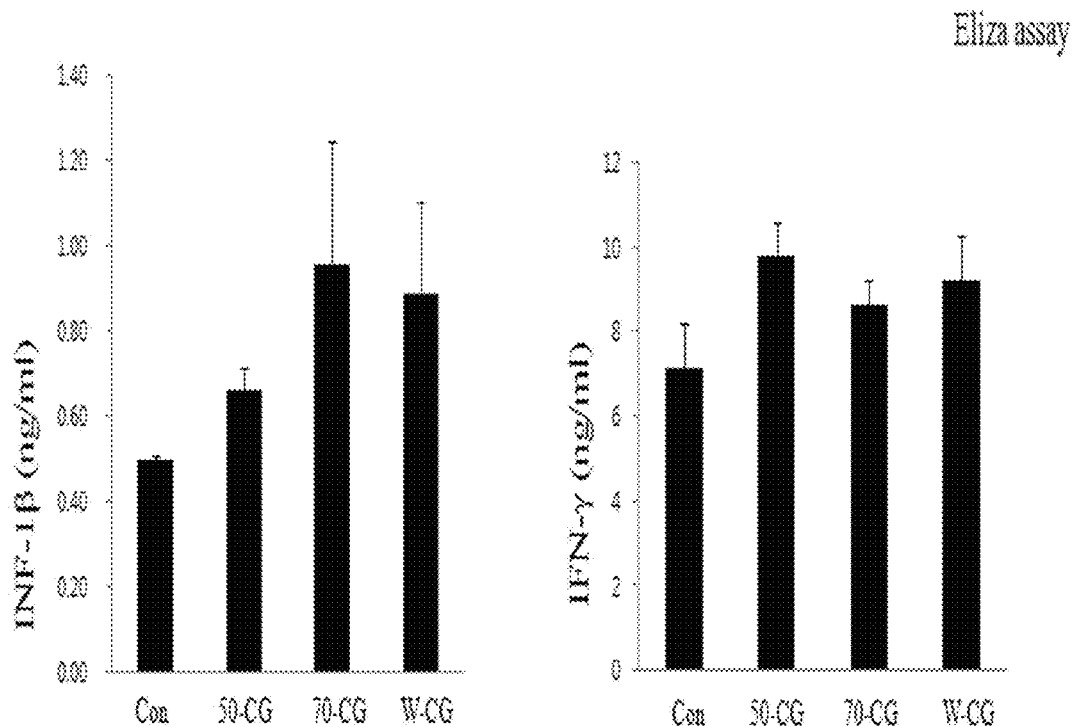
FIG. 24 is a diagram illustrating the expression of cytokine (IL-2, IL-4, and IL-10) in APP/PS1 mice treated with the centipede grass ethylacetate-methanol fraction.

The levels of INF-1β and INF-γ were also high in the mouse groups treated with the centipede grass ethylacetate-50% methanol fraction, the centipede grass ethylacetate-70% methanol fraction, and the centipede grass ethylacetate-100% methanol fraction, compared with those of the control group (FIG. 24).

Figure 25:
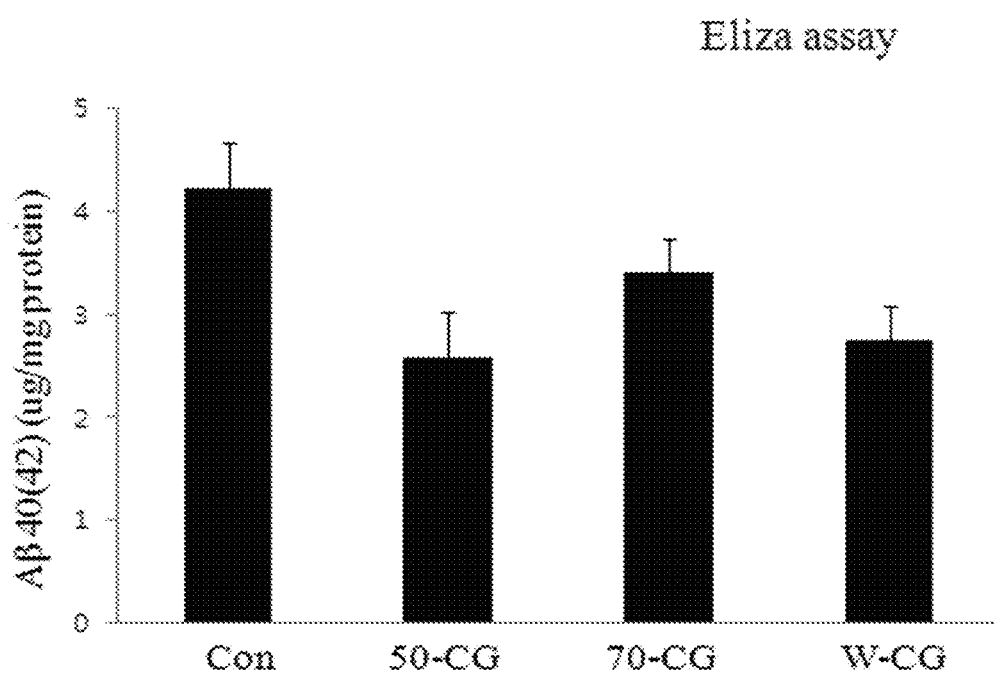
FIG. 25 is a diagram illustrating the expression of Aβ in APP/PS1 mice treated with the centipede grass ethylacetate-methanol fraction.

In the meantime, the level of amyloid-beta was low in the mouse groups treated with the centipede grass ethylacetate-50% methanol fraction, the centipede grass ethylacetate-70% methanol fraction, and the centipede grass ethylacetate-100% methanol fraction, compared with those of the control group (FIG. 25).

Experimental Example 15: Histological Analysis (H-E Staining) with the Test Animal Treated with Centipede Grass Ethylacetate-Methanol Fraction The lesions of the brain tissues of the mice treated with the centipede grass ethylacetate-methanol fraction and APP mice were examined by H-E staining.

Particularly, the brain tissues were extracted and fixed in 4% neutral buffered paraformaldehyde for 48~72 hours. The fixed tissues were washed to eliminate the fixing solution. Then, the tissues were reacted in 70% ethanol for 1 hour, in 80% ethanol for 1 hour, in 90% ethanol for 1 hour, and in 95% ethanol for 1 hour, and in 100% ethanol for 2 hours and in xylene for 2 hours, leading to dehydration and vitrification. The tissues were formatted in the paraffin embedding center (Leica, Wetzlar, Germany). The paraffin block was sliced into 5 μm thick sections. The sliced tissue sections proceeded to deparaffinization and hydration serially in xylene for 15 minutes, twice, in 100% ethanol for 3 minutes, in 95% ethanol for 3 minutes, in 90% ethanol for 3 minutes, in 80% ethanol for 3 minutes, and in 70% ethanol for 3 minutes, followed by staining with hematoxylin for 10 minutes and with eosin for 1 minute. The tissues were sealed by using permount, and then observed under optical microscope.

Figure 26:
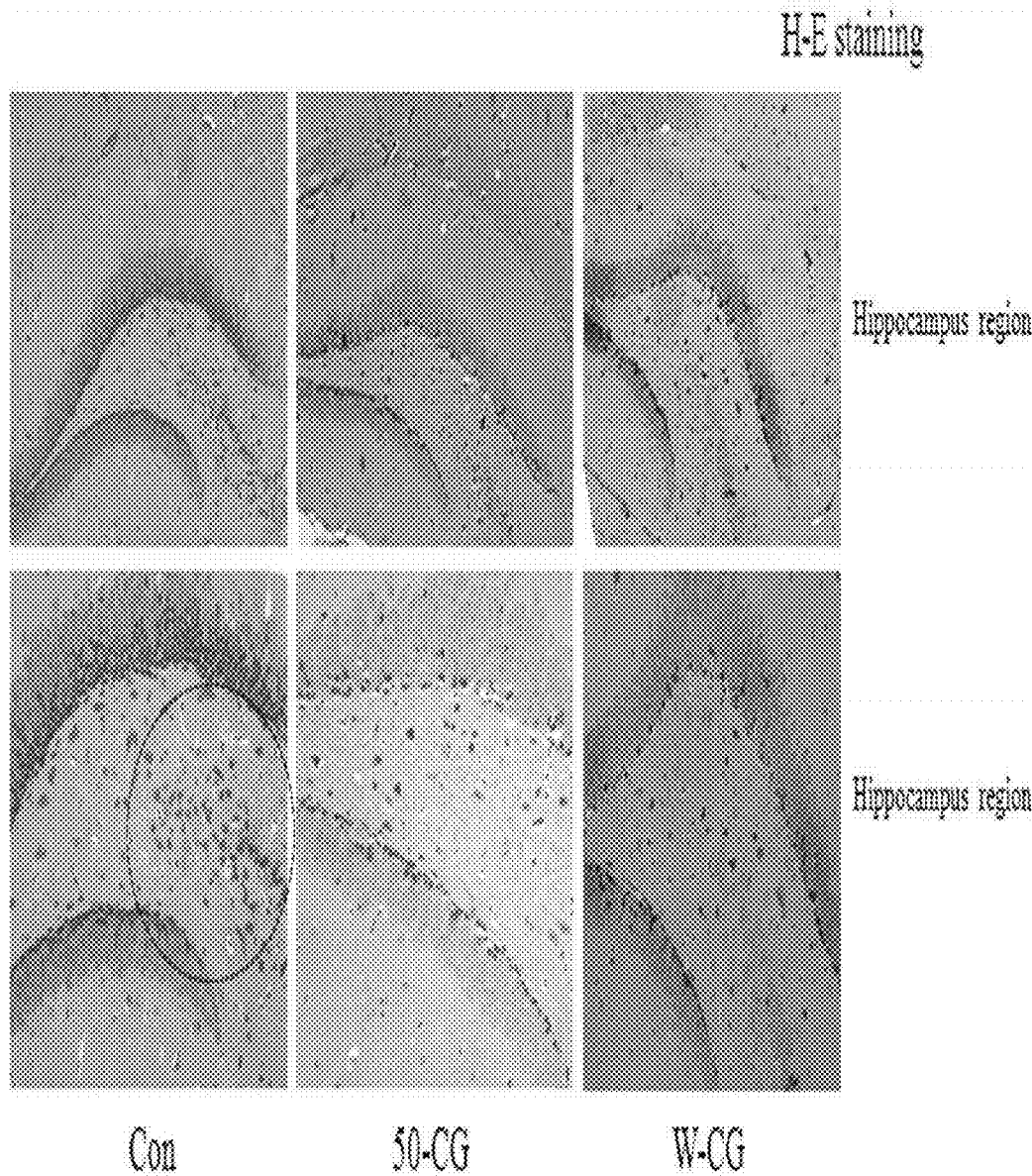
FIG. 26 is a diagram illustrating the inhibition of apoptosis in the brain tissue, confirmed by the strong cell death signal in the hippocampus of the mouse treated with the centipede grass ethylacetate-methanol fraction.

As a result, cell death signal was stronger in the hippocampus of the mouse treated with the centipede grass ethylacetate-50% methanol fraction or the centipede grass ethylacetate-100% methanol fraction than in the APP mouse, suggesting that the fraction could inhibit cell death in the brain tissue (FIG. 26).

Figure 27:
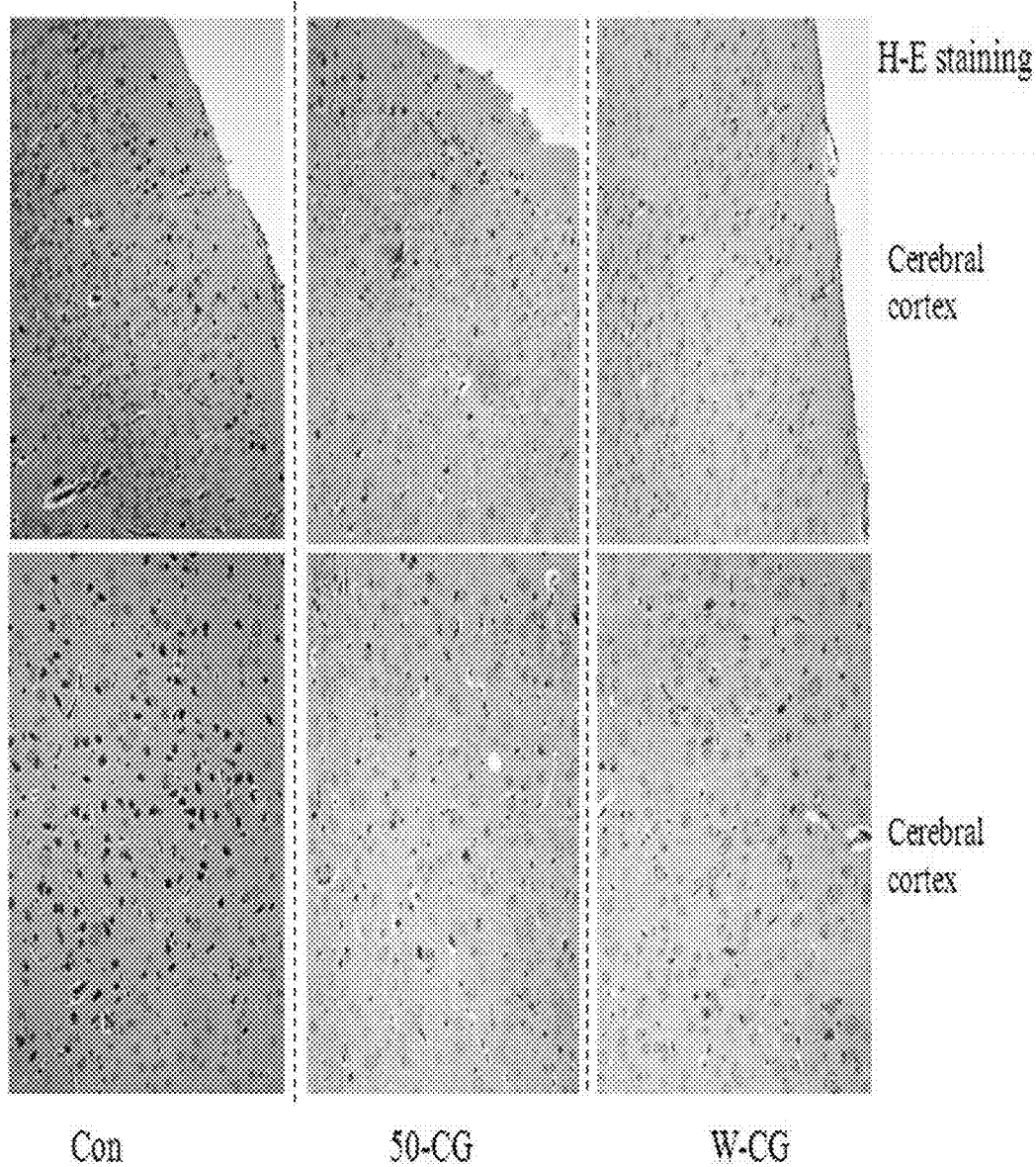
FIG. 27 is a diagram illustrating the suppression of progressive degeneration, confirmed by the strong cell death signal in the cortex of the mouse treated with the centipede grass ethylacetate-methanol fraction.

In addition, cell death signal was stronger in the cortex of the mouse treated with the centipede grass ethylacetate-50% methanol fraction or the centipede grass ethylacetate-100% methanol fraction than in the APP mouse, suggesting that the fraction could suppress the progressive degeneration (FIG. 27).

Experimental Example 16: Immunohistochemical Analysis with the Test Animal Treated with Centipede Grass Ethylacetate-Methanol Fraction Aβ was investigated in the cortex and the hippocampus of both APP mouse and the mouse treated with the centipede grass ethylacetate-methanol fraction by immunohistochemical analysis using Aβ antibody.

Particularly, the brain tissues were extracted and fixed in 4% neutral buffered paraformaldehyde for 48~72 hours. The fixed tissues were washed to eliminate the fixing solution. Then, the tissues were reacted in 70% ethanol for 1 hour, in 80% ethanol for 1 hour, in 90% ethanol for 1 hour, and in 95% ethanol for 1 hour, and in 100% ethanol for 2 hours and in xylene for 2 hours, leading to dehydration and vitrification. The tissues were formatted in the paraffin embedding center (Leica, Wetzlar, Germany). The paraffin block was sliced into 10 μm thick sections. The sliced tissue sections proceeded to deparaffinization and hydration serially in xylene, 100% ethanol, 95% ethanol, 90% ethanol, 80% ethanol, and 70% ethanol. The tissue sections were washed with 0.1 M sodium phosphate buffer (0.1 M PB) for 5 minutes three times, and then reacted with the primary antibody 6E10 (Covance, 1:50) at room temperature for 2 hours. The secondary antibody was prepared by diluting FITC conjugate antibody (Sigma) at the ratio of 1:100~1:200, which was reacted with the tissue section for 2 hours. For the dilution of each antibody, 0.1 M PB containing 1% normal goat serum (Sigma) and 0.3% Triton X-100 (Sigma) was used. The washing in each stage of antibody treatment was performed with PBS for 5 minutes three times each. The cells emitting fluorescence were regarded as positive cells, whose distribution was therefore examined.

Figure 28:
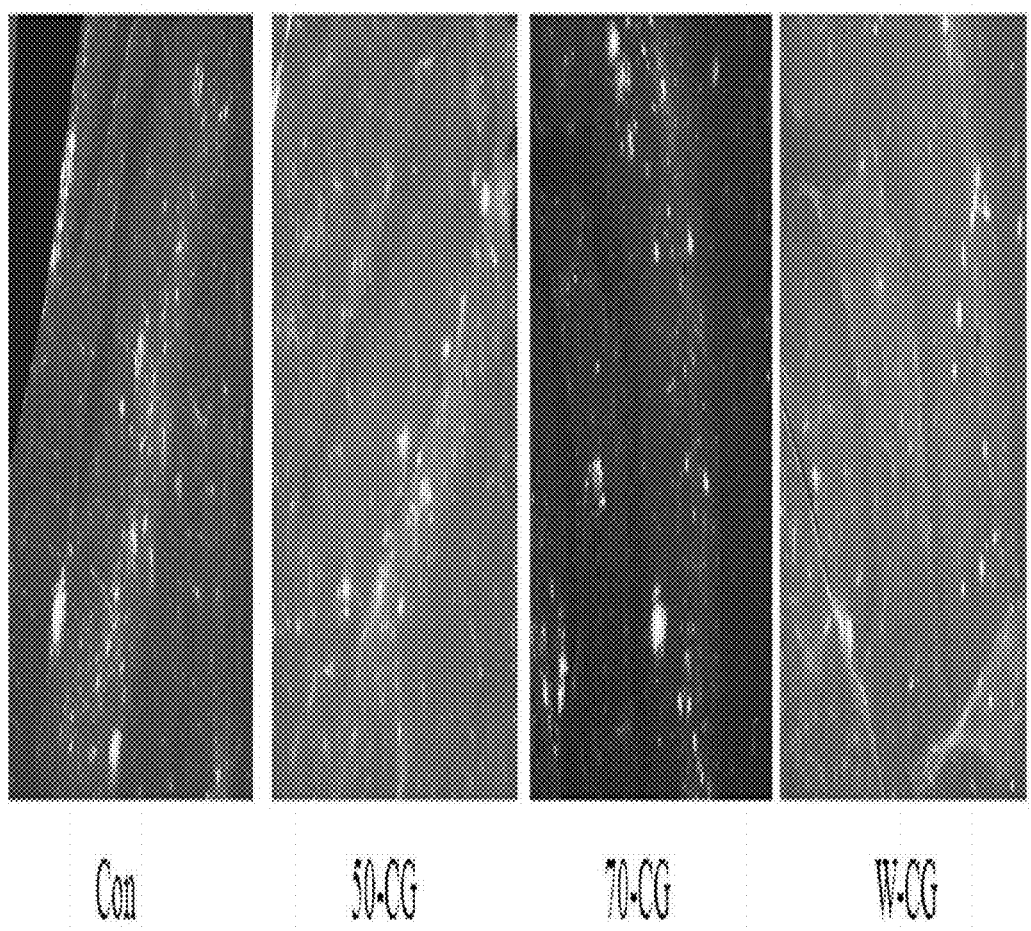
FIG. 28 is a diagram illustrating the decrease of Aβ in the hippocampus of APP mouse and the mouse treated with the centipede grass ethylacetate-methanol, confirmed by immunohistochemical assay using Aβ antibody.

As a result, Aβ was significantly reduced in the mouse treated with the centipede grass ethylacetate-50% methanol fraction and the centipede grass ethylacetate-100% methanol fraction (FIG. 28).

Figure 29:
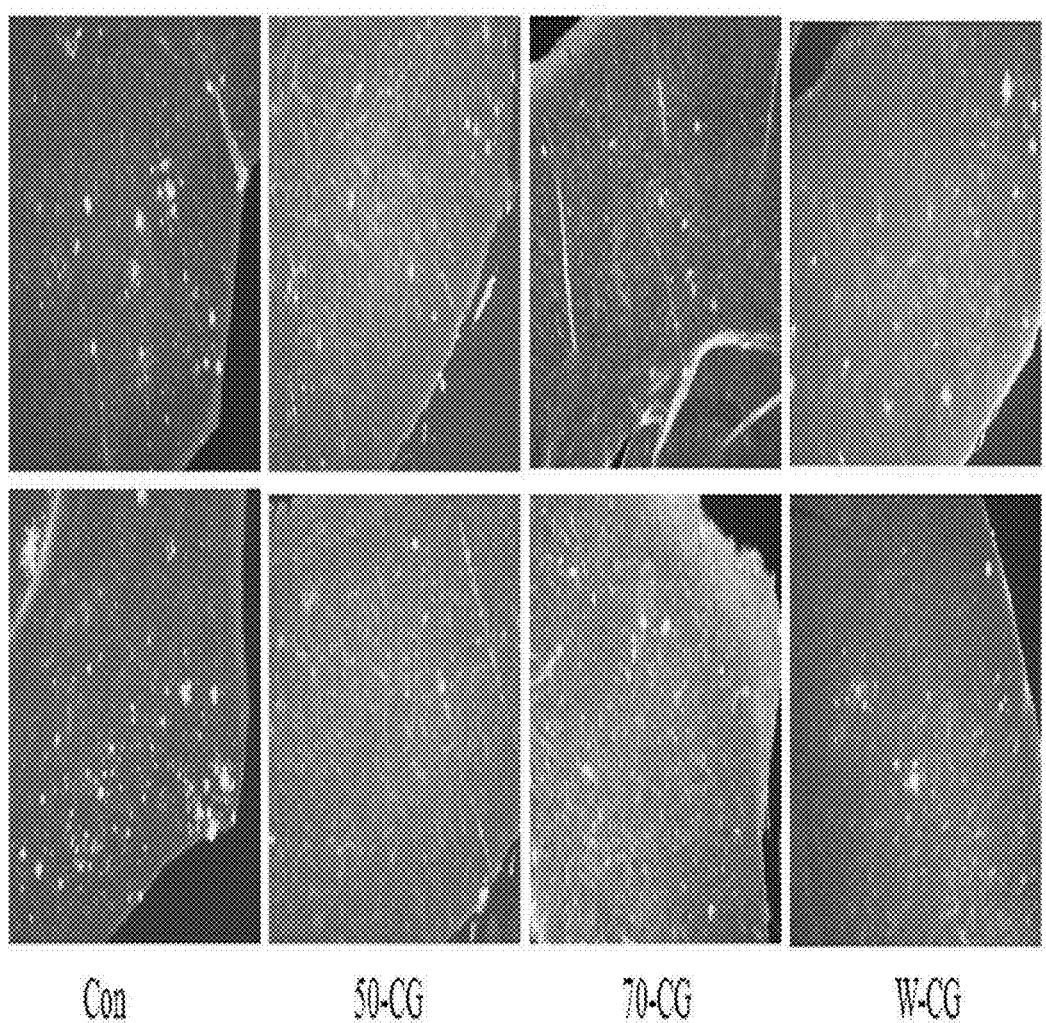
FIG. 29 is a diagram illustrating the decrease of Aβ in the cortex of APP mouse and the mouse treated with the centipede grass ethylacetate-methanol, confirmed by immunohistochemical assay using Aβ antibody.

The above results confirming that Aβ was significantly reduced in the mouse treated with the centipede grass ethylacetate-50% methanol fraction, the centipede grass ethylacetate-70% methanol fraction, and the centipede grass ethylacetate-100% methanol fraction suggested that the centipede grass ethylacetate-methanol fraction could inhibit the accumulation of amyloid-beta in the cortex of the mouse brain (FIG. 29).

Preparative Example 1: Preparation of a Composition for Preventing and Treating Diabetes and Dementia Comprising Centipede Grass Extract as an Active Ingredient Manufacturing Example 1: Preparation of Pharmaceutical Formulations <1-1> Preparation of Powders

| | |
|---|---|
| Centipede grass methanol extract of Example <1-1> | 0.1 g |
| Lactose | 1.5 g |
| Talc | 0.5 g |

Powders were prepared by mixing all the above components, which were filled in airtight packs according to the conventional method for preparing powders.

<1-2> Preparation of Tablets

Tablets comprising the centipede grass extract of the present invention as an active ingredient were prepared according to the composition shown in Table 2.

TABLE 2

| Constituent | Content (weight part) |
|---|---|
| Centipede grass extract | 250 |
| Lactose | 175.9 |
| Potato starch | 180 |
| Colloidal silicic acid | 32 |
| 10% gelatin solution | 5 |
| Starch | 160 |
| Talc | 50 |
| Magnesium stearate | 5 |

250 g of the extract of the present invention, 175.9 g of lactose, 180 g of potato starch and 32 g of colloidal silicic acid were all mixed together. 10% gelatin solution was added to the mixture, which was then pulverized and filtered with 14-mesh sieve. The pulverized mixture was dried, to which 160 g of potato starch, 50 g of talc and 5 g of magnesium stearate were added to prepare tablets.

<1-3> Preparation of Capsules

| | |
|---|---|
| Centipede grass methanol extract of Example <1-1> | 0.1 g |
| Corn starch | 5 g |
| Carboxy cellulose | 4.9 g |

Capsules were prepared by mixing all the above components, which filled hard capsules according to the conventional method for preparing capsules.

<1-4> Preparation of Injectable Solutions

| | |
|---|---|
| Centipede grass methanol extract of Example <1-1> | 0.1 g |
| Sterilized distilled water | proper amount |
| pH regulator | proper amount |

Injectable solutions were prepared by mixing all the above components, putting the mixture into 2 ml ampoules and sterilizing thereof by the conventional method for preparing injectable solutions.

<1-5> Preparation of Liquid Formulations

| | |
|---|---|
| Centipede grass methanol extract of Example <1-1> | 0.1 g |
| Isomerized sugar | 10 g |
| Mannitol | 5 g |
| Purified water | proper amount |

All the above components were dissolved in purified water. After adding lemon flavor, total volume was adjusted to be 100 ml by adding purified water. Liquid formulations were prepared by putting the mixture into brown bottles and sterilizing thereof by the conventional method for preparing liquid formulations.

<1-6> Preparation of Syrups

Syrups comprising the centipede grass extract of the present invention as an active ingredient were prepared according to the composition shown in Table 3.

TABLE 3

| Constituent | Content (weight part) |
|---|---|
| Centipede grass extract | 2 |
| Saccharin | 0.8 |
| Sucrose | 25.4 |
| Glycerin | 8 |
| Feed flavor | 0.04 |
| Ethanol | 4 |
| Sorbic acid | 0.4 |
| Distilled water | 60 |

Manufacturing Example 2: Preparation of Health Food Comprising Centipede Grass Extract as an Active Ingredient <2-1> Preparation of Flour Food

| | |
|---|---|
| Centipede grass methanol extract of Example <1-1> | 0.1 g |

0.5~5.0 weight part of the centipede grass water extract of Example <1-3> was added to the flour. Health enhancing foods such as bread, cake, cookies, crackers and noodles were prepared with the flour mixture according to the conventional method.

<2-2> Preparation of Soups and Gravies 0.1~5.0 weight part of the centipede grass water extract of Example <1-3> was added to soups and gravies. Health enhancing meat products, soups and gravies were prepared with this mixture by the conventional method.

<2-3> Preparation of Ground Beef

Health enhancing ground beef was prepared by mixing 10 weight part of the centipede grass water extract of Example <1-3> with ground beef according to the conventional method.

<2-4> Preparation of Dairy Products

5~10 weight part of the centipede grass water extract of Example <1-3> was added to milk. Health enhancing dairy products such as butter and ice cream were prepared with the milk mixture according to the conventional method.

<2-5> Preparation of Sun-Sik

Brown rice, barley, glutinous rice and Yulmu (Job's tears) were gelatinized according to the conventional method, dried and pulverized to obtain 60-mesh powders.

Black soybean, black sesame and wild sesame were steamed and dried according to the conventional method and pulverized to obtain 60-mesh powders.

The centipede grass water extract of Example <1-3> was concentrated under reduced pressure, spray-dried and pulverized to obtain 60-mesh dry powders.

Sun-Sik was prepared by mixing the dry powders of the grains, seeds and the centipede grass water extract of Example <1-3> according to the below ratio.

Grains (brown rice: 30 weight part, Yulmu: 15 weight part, barley: 20 weight part, glutinous rice: 10 weight part), Seeds (wild sesame: 7 weight part, black soybean: 8 weight part, black sesame: 7 weight part), Dry powders of the centipede grass water extract of Example <1-3>(3 weight part),

*Ganoderma lucidum* (0.5 weight part),

*Rehmannia glutinosa* (0.5 weight part)

Manufacturing Example 3: Preparation of Functional Beverages Comprising Centipede Grass Extract as an Active Ingredient <3-1> Preparation of Health Beverages The centipede grass extract of the present invention (5 g) was mixed with liquid fructose (0.5%), oligosaccharide (2%), sugar (2%), salt (0.5%), and water (75%). After mixing completely, the mixture was sterilized instantly and filled small containers such as glass bottles, pet bottles, etc, to prepare health beverages.

<3-2> Preparation of Vegetable Juice

Health enhancing vegetable juice was prepared by adding 5 g of the centipede grass extract of the present invention to 1,000 ml of tomato or carrot juice according to the conventional method.

<3-3> Preparation of Fruit Juice

Health enhancing fruit juice was prepared by adding 1 g of the centipede grass extract of the present invention to 1,000 ml of apple or grape juice according to the conventional method.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for treating diabetes comprising administering to a subject in need thereof an effective amount of a centipede grass (*Eremochloa ophiuroides*) extract, wherein the extract is prepared by a method comprising the steps of:
   (a) extracting centipede grass leaves with methanol to produce a methanol extract,
   (b) concentrating the methanol extract and suspending it in water to produce a suspension,
   (c) adding n-hexane to the suspension to yield a soluble layer and a water layer, then discarding the soluble layer,
   (d) combining the water layer with ethyl acetate to produce an ethyl acetate fraction, and
   (e) mixing the ethyl acetate fraction with 50-70% methanol to obtain a mixture, and subjecting the mixture to column chromatography to obtain the centipede grass extract.

2. The method according to claim 1, wherein the diabetes is type I diabetes.

3. The method according to claim 1, wherein the diabetes is type II diabetes.

4. A method for regulating blood glucose comprising administering to a subject in need thereof an effective amount of a centipede grass (*Eremochloa ophiuroides*) extract,
   wherein the extract is prepared by a method comprising the steps of:
   (a) extracting centipede grass leaves with methanol to produce a methanol extract,
   (b) concentrating the methanol extract and suspending it in water to produce a suspension,
   (c) adding n-hexane to the suspension to yield a soluble layer and a water layer, then discarding the soluble layer,
   (d) combining the water layer with ethyl acetate to produce an ethyl acetate fraction, and
   (e) mixing the ethyl acetate fraction with 50-70% methanol to obtain a mixture, and subjecting the mixture to column chromatography to obtain the centipede grass extract.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: IL1a_F

<400> SEQUENCE: 1
aggagagccg ggtgacagta                                                    20

<210> SEQ ID NO 2
<211> LENGTH: 23
<212> TYPE: DNA
<213> ORGANISM: Artificial Sequence
<220> FEATURE:
<223> OTHER INFORMATION: IL1a_R

<400> SEQUENCE: 2
aactcagccg tctcttcttc aga                                                23

<210> SEQ ID NO 3
<211> LENGTH: 23
<212> TYPE: DNA
<213> ORGANISM: Artificial Sequence
<220> FEATURE:
<223> OTHER INFORMATION: IFNg_F

<400> SEQUENCE: 3
tgaacgctac acactgcatc ttg                                                23

<210> SEQ ID NO 4
<211> LENGTH: 28
<212> TYPE: DNA
<213> ORGANISM: Artificial Sequence
<220> FEATURE:
<223> OTHER INFORMATION: IFNg_R

<400> SEQUENCE: 4
gttattcaga ctttctaggc tttcaatg                                           28

<210> SEQ ID NO 5
<211> LENGTH: 23
<212> TYPE: DNA
<213> ORGANISM: Artificial Sequence
<220> FEATURE:
<223> OTHER INFORMATION: IL6_F

<400> SEQUENCE: 5
gaggatacca ctcccaacag acc                                                23

<210> SEQ ID NO 6
<211> LENGTH: 24
<212> TYPE: DNA
<213> ORGANISM: Artificial Sequence
<220> FEATURE:
<223> OTHER INFORMATION: IL6_R

<400> SEQUENCE: 6
aagtgcatca tcgttgttca taca                                               24